United States Patent
Wondka et al.

(10) Patent No.: US 8,925,545 B2
(45) Date of Patent: *Jan. 6, 2015

(54) METHODS AND DEVICES FOR TREATING SLEEP APNEA

(75) Inventors: Anthony Wondka, Thousand Oaks, CA (US); Gregory Kapust, San Ramon, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1511 days.

This patent is subject to a terminal disclaimer.

(21) Appl. No.: 12/239,719

(22) Filed: Sep. 26, 2008

(65) Prior Publication Data
US 2009/0151719 A1    Jun. 18, 2009

Related U.S. Application Data

(60) Provisional application No. 60/960,362, filed on Sep. 26, 2007.

(51) Int. Cl.
*A61M 16/04* (2006.01)
*A61M 16/10* (2006.01)
(Continued)

(52) U.S. Cl.
CPC ....... *A61M 16/0096* (2013.01); *A61M 16/0051* (2013.01); *A61M 16/0465* (2013.01);
(Continued)

(58) Field of Classification Search
CPC ............... A61M 2016/0021; A61M 16/00; A61M 2016/0027; A61M 16/0051; A61M 2016/0036
USPC ............. 128/200.24, 200.26, 204.18, 204.21, 128/204.23, 205.25, 206.21, 206.29, 128/207.14, 207.18; 604/256, 523, 604/533–539, 284, 93.01, 95.02, 118, 264, 604/258, 94.01
See application file for complete search history.

(56) References Cited

U.S. PATENT DOCUMENTS

| 50,641 A | 10/1865 | Stone |
| 428,592 A | 5/1890 | Chapman |

(Continued)

FOREIGN PATENT DOCUMENTS

| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Annette Dixon
(74) *Attorney, Agent, or Firm* — Stetina Brunda Garred & Brucker

(57) ABSTRACT

A ventilation apparatus for treating sleep apnea is provided. A ventilator controlled by a control system may deliver ventilation gas through a ventilation gas delivery circuit to a ventilation catheter and a distal tip on the ventilation catheter. One or more sensors may detect a breathing cycle and the control system may operate the ventilator in synchrony with the breathing cycle. The distal tip may deliver the ventilation gas superiorly from the transtracheal ventilation catheter towards an upper airway, inferiorly from the transtracheal ventilation catheter towards a lung, or a combination of both. The ventilation catheter may be a transtracheal catheter, a trans-oral catheter or a trans-nasal catheter.

54 Claims, 16 Drawing Sheets

(51) Int. Cl.
    *A61B 5/08*           (2006.01)
    *A61M 16/00*        (2006.01)
    *A61M 16/06*        (2006.01)

(52) U.S. Cl.
    CPC ........... *A61M 16/0666* (2013.01); *A61M 16/10*
        (2013.01); *A61M 2016/0021* (2013.01); *A61M*
        *2016/0027* (2013.01); *A61M 2016/0036*
        (2013.01); *A61M 2205/17* (2013.01); *A61M*
        *2205/332* (2013.01); *A61M 2205/3569*
        (2013.01); *A61M 2205/3592* (2013.01); *A61M*
        *2230/10* (2013.01); *A61M 2230/205* (2013.01);
        *A61M 2230/432* (2013.01); *A61M 2230/60*
        (2013.01)
    USPC ............. 128/204.23; 128/204.18; 128/204.21

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,788,326 A * | 1/1974 | Jacobs ..................... 128/207.15 |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |

(56) References Cited

U.S. PATENT DOCUMENTS

| | | |
|---|---|---|
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A * | 8/1993 | Atkins ..................... 128/204.18 |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A * | 9/1996 | Smith et al. ............... 128/204.26 |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |

(56) References Cited

U.S. PATENT DOCUMENTS

| | | | |
|---|---|---|---|
| 5,687,713 A | 11/1997 | Bahr et al. | |
| 5,687,714 A | 11/1997 | Kolobow et al. | |
| 5,687,715 A | 11/1997 | Landis et al. | |
| 5,690,097 A | 11/1997 | Howard et al. | |
| 5,692,497 A | 12/1997 | Schnitzer et al. | |
| 5,697,364 A | 12/1997 | Chua et al. | |
| 5,704,345 A | 1/1998 | Berthon-Jones | |
| 5,711,296 A | 1/1998 | Kolobow | |
| 5,715,812 A | 2/1998 | Deighan et al. | |
| 5,715,815 A | 2/1998 | Lorenzen et al. | |
| 5,720,278 A | 2/1998 | Lachmann et al. | |
| 5,735,268 A | 4/1998 | Chua et al. | |
| 5,735,272 A | 4/1998 | Dillon et al. | |
| 5,740,796 A | 4/1998 | Skog | |
| 5,752,511 A | 5/1998 | Simmons et al. | |
| 5,762,638 A | 6/1998 | Shikani et al. | |
| 5,791,337 A | 8/1998 | Coles et al. | |
| 5,819,723 A | 10/1998 | Joseph | |
| 5,826,579 A | 10/1998 | Remmers et al. | |
| 5,845,636 A | 12/1998 | Gruenke et al. | |
| 5,865,173 A | 2/1999 | Froehlich | |
| 5,865,174 A | 2/1999 | Kloeppel | |
| 5,881,723 A | 3/1999 | Wallace et al. | |
| 5,904,648 A | 5/1999 | Arndt et al. | |
| 5,906,204 A | 5/1999 | Beran et al. | |
| 5,911,756 A | 6/1999 | Debry | |
| 5,915,379 A | 6/1999 | Wallace et al. | |
| 5,915,381 A | 6/1999 | Nord | |
| 5,918,597 A | 7/1999 | Jones et al. | |
| 5,921,238 A | 7/1999 | Bourdon | |
| 5,921,942 A | 7/1999 | Remmers et al. | |
| 5,921,952 A | 7/1999 | Desmond, III et al. | |
| 5,927,276 A | 7/1999 | Rodriguez | |
| 5,928,189 A | 7/1999 | Phillips et al. | |
| 5,931,160 A | 8/1999 | Gilmore et al. | |
| 5,931,162 A | 8/1999 | Christian | |
| 5,937,853 A | 8/1999 | Strom | |
| 5,937,855 A | 8/1999 | Zdrojkowski et al. | |
| 5,938,118 A | 8/1999 | Cooper | |
| 5,954,050 A * | 9/1999 | Christopher | 128/204.23 |
| 5,957,136 A | 9/1999 | Magidson et al. | |
| 5,964,223 A | 10/1999 | Baran | |
| 5,975,077 A | 11/1999 | Hofstetter et al. | |
| 5,975,081 A | 11/1999 | Hood et al. | |
| 5,979,440 A | 11/1999 | Honkonen et al. | |
| 5,989,193 A | 11/1999 | Sullivan | |
| 6,000,396 A | 12/1999 | Melker et al. | |
| 6,019,101 A | 2/2000 | Cotner et al. | |
| 6,039,696 A | 3/2000 | Bell | |
| 6,050,260 A | 4/2000 | Daniell et al. | |
| 6,076,519 A | 6/2000 | Johnson | |
| 6,085,747 A | 7/2000 | Axe et al. | |
| 6,091,973 A | 7/2000 | Colla et al. | |
| 6,093,169 A | 7/2000 | Cardoso | |
| 6,105,575 A | 8/2000 | Estes et al. | |
| 6,109,264 A | 8/2000 | Sauer | |
| 6,112,746 A | 9/2000 | Kwok et al. | |
| 6,119,694 A | 9/2000 | Correa et al. | |
| 6,120,460 A | 9/2000 | Abreu | |
| 6,123,668 A | 9/2000 | Abreu | |
| 6,131,571 A | 10/2000 | Lampotang et al. | |
| 6,135,970 A | 10/2000 | Kadhiresan et al. | |
| 6,152,132 A | 11/2000 | Psaros | |
| 6,152,134 A | 11/2000 | Webber et al. | |
| 6,158,432 A | 12/2000 | Biondi et al. | |
| 6,192,883 B1 | 2/2001 | Miller, Jr. | |
| 6,203,502 B1 | 3/2001 | Hilgendorf et al. | |
| 6,213,119 B1 | 4/2001 | Brydon et al. | |
| 6,213,955 B1 | 4/2001 | Karakasoglu et al. | |
| 6,220,244 B1 | 4/2001 | McLaughlin | |
| 6,224,560 B1 | 5/2001 | Gazula et al. | |
| 6,227,200 B1 | 5/2001 | Crump et al. | |
| 6,247,470 B1 | 6/2001 | Ketchedjian | |
| 6,269,811 B1 | 8/2001 | Duff et al. | |
| 6,269,812 B1 | 8/2001 | Wallace et al. | |
| 6,273,859 B1 | 8/2001 | Remmers et al. | |
| 6,286,508 B1 | 9/2001 | Remmers et al. | |
| D449,376 S | 10/2001 | McDonald et al. | |
| D449,883 S | 10/2001 | McDonald et al. | |
| 6,298,850 B1 | 10/2001 | Argraves | |
| 6,305,374 B1 | 10/2001 | Zdrojkowski et al. | |
| 6,314,957 B1 | 11/2001 | Boissin et al. | |
| 6,315,739 B1 | 11/2001 | Merilainen et al. | |
| D451,598 S | 12/2001 | McDonald et al. | |
| 6,328,038 B1 | 12/2001 | Kessler et al. | |
| 6,328,753 B1 | 12/2001 | Zammit | |
| 6,332,463 B1 | 12/2001 | Farrugia et al. | |
| 6,345,619 B1 | 2/2002 | Finn | |
| 6,357,438 B1 | 3/2002 | Hansen | |
| 6,357,440 B1 | 3/2002 | Hansen et al. | |
| 6,360,741 B2 | 3/2002 | Truschel | |
| 6,360,745 B1 | 3/2002 | Wallace et al. | |
| 6,363,933 B1 | 4/2002 | Berthon-Jones | |
| 6,367,474 B1 | 4/2002 | Berthon-Jones et al. | |
| 6,369,838 B1 | 4/2002 | Wallace et al. | |
| 6,371,114 B1 | 4/2002 | Schmidt et al. | |
| 6,378,520 B1 | 4/2002 | Davenport | |
| 6,390,091 B1 | 5/2002 | Banner et al. | |
| 6,394,088 B1 | 5/2002 | Frye et al. | |
| 6,398,739 B1 | 6/2002 | Sullivan et al. | |
| 6,418,928 B1 | 7/2002 | Bordewick et al. | |
| 6,422,240 B1 | 7/2002 | Levitsky et al. | |
| 6,423,001 B1 | 7/2002 | Abreu | |
| 6,427,690 B1 | 8/2002 | McCombs et al. | |
| 6,431,172 B1 | 8/2002 | Bordewick | |
| 6,439,228 B1 | 8/2002 | Hete et al. | |
| 6,439,229 B1 | 8/2002 | Du et al. | |
| 6,439,234 B1 | 8/2002 | Curti et al. | |
| 6,439,235 B1 | 8/2002 | Larquet et al. | |
| 6,450,164 B1 | 9/2002 | Banner et al. | |
| 6,450,166 B1 | 9/2002 | McDonald et al. | |
| 6,457,472 B1 | 10/2002 | Schwartz et al. | |
| 6,467,477 B1 | 10/2002 | Frank et al. | |
| 6,478,026 B1 | 11/2002 | Wood | |
| 6,494,202 B2 | 12/2002 | Farmer | |
| 6,494,206 B1 | 12/2002 | Bergamaschi et al. | |
| 6,505,623 B1 | 1/2003 | Hansen | |
| 6,505,624 B1 | 1/2003 | Campbell, Sr. | |
| 6,516,801 B2 | 2/2003 | Boussignac | |
| 6,520,176 B1 | 2/2003 | Dubois et al. | |
| 6,520,183 B2 | 2/2003 | Amar | |
| 6,530,373 B1 | 3/2003 | Patron et al. | |
| 6,532,958 B1 | 3/2003 | Buan et al. | |
| 6,532,960 B1 | 3/2003 | Yurko | |
| 6,536,432 B2 | 3/2003 | Truschel | |
| 6,536,436 B1 | 3/2003 | McGlothen | |
| 6,550,478 B2 | 4/2003 | Remmers et al. | |
| 6,553,992 B1 | 4/2003 | Berthon-Jones et al. | |
| 6,561,188 B1 | 5/2003 | Ellis | |
| 6,561,193 B1 | 5/2003 | Noble | |
| 6,564,797 B1 | 5/2003 | Mechlenburg et al. | |
| 6,564,800 B1 | 5/2003 | Olivares | |
| 6,568,391 B1 | 5/2003 | Tatarek et al. | |
| 6,571,794 B1 | 6/2003 | Hansen | |
| 6,571,796 B2 | 6/2003 | Banner et al. | |
| 6,571,798 B1 | 6/2003 | Thornton | |
| 6,575,159 B1 | 6/2003 | Frye et al. | |
| 6,575,944 B1 | 6/2003 | McNary et al. | |
| 6,584,973 B1 | 7/2003 | Biondi et al. | |
| 6,588,422 B1 | 7/2003 | Berthon-Jones et al. | |
| 6,588,423 B1 | 7/2003 | Sinderby | |
| 6,591,834 B1 | 7/2003 | Colla et al. | |
| 6,591,835 B1 | 7/2003 | Blanch | |
| 6,595,207 B1 | 7/2003 | McDonald et al. | |
| 6,595,215 B2 | 7/2003 | Wood | |
| 6,609,517 B1 | 8/2003 | Estes et al. | |
| 6,622,726 B1 | 9/2003 | Du | |
| 6,626,174 B1 | 9/2003 | Genger et al. | |
| 6,626,175 B2 | 9/2003 | Jafari et al. | |
| 6,629,525 B2 | 10/2003 | Hill et al. | |
| 6,629,527 B1 | 10/2003 | Estes et al. | |
| 6,629,529 B2 | 10/2003 | Arnott | |
| 6,631,919 B1 | 10/2003 | West et al. | |
| 6,634,356 B1 | 10/2003 | O'Dea et al. | |

(56) References Cited

U.S. PATENT DOCUMENTS

| | | |
|---|---|---|
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |

(56) References Cited

U.S. PATENT DOCUMENTS

| | | | |
|---|---|---|---|
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034721 A1 | 2/2005 | Freitag |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |

(56) References Cited

U.S. PATENT DOCUMENTS

| | | |
|---|---|---|
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1* | 12/2005 | Deane et al. ............ 128/204.23 |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunaratnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |

(56) References Cited

U.S. PATENT DOCUMENTS

| | | |
|---|---|---|
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1* | 10/2010 | Wondka et al. ........... 128/203.12 |
| 2010/0252039 A1* | 10/2010 | Cipollone et al. ........ 128/204.23 |
| 2010/0252040 A1* | 10/2010 | Kapust et al. ............. 128/204.23 |
| 2010/0252041 A1 | 10/2010 | Kapust et al. |
| 2010/0252042 A1* | 10/2010 | Kapust et al. ............. 128/204.23 |
| 2010/0252043 A1 | 10/2010 | Freitag |
| 2010/0252044 A1 | 10/2010 | Duquette et al. |
| 2010/0269834 A1* | 10/2010 | Freitag et al. ............. 128/207.14 |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | 05200116 | 8/1993 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |

(56) References Cited

FOREIGN PATENT DOCUMENTS

| WO | WO-2010/041966 | 4/2010 |
|----|----|----|
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-22.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.

(56) References Cited

OTHER PUBLICATIONS

Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.

Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," *Chest*, 1983: 83(1), pp. 144-145.

(56) References Cited

OTHER PUBLICATIONS

Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.
Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
Japanese Office Action, 2 Pages, Patent Application No. 2010-527224.
English Translation of Japanese Office Action, 2 Pages, Patent Application No. 2010-527224.
Abstract to JP05200116, Espacenet, 2 Pages.
Partial Translation of JP05200116, 2 Pages.

\* cited by examiner

SECTION A-A

SECTION B-B

METHODS AND DEVICES FOR TREATING SLEEP APNEA

CROSS-REFERENCE TO RELATED APPLICATIONS

This application claims priority to U.S. Provisional Patent Application No. 60/960,362, filed Sep. 26, 2007, the content of which is incorporated by reference herein in its entirety. This application incorporates by reference U.S. Non-Provisional patent application Ser. No. 10/870,849, filed Jun. 17, 2004, and now issued U.S. Pat. No. 7,588,033, and U.S. Non-Provisional patent application Ser. No. 10/177,803 filed Feb. 4, 2004, and now issued as U.S. Pat. No. 7,487,778, the contents of which are incorporated by reference herein in their entireties.

FIELD OF THE INVENTION

The present invention relates to ventilation therapy for persons suffering from breathing disorders, such as obstructive sleep apnea and central sleep apnea. More specifically, the present invention relates to methods and apparatus for restoring, augmenting, or providing ventilation to the lungs using a ventilation catheter.

BACKGROUND OF THE INVENTION

There are two forms of sleep apnea known in the art. Central sleep apnea (CSA) is the loss of neurological drive to breathe. Obstructive sleep apnea (OSA) syndrome, the more common form of the two, is a physical obstruction of the oropharyngeal area of the upper airway. Due to morphology and neuromuscular tone, the tissue structures can close and remain closed for a prolonged period of time during sleep. These apneic episodes are followed by sudden attempts to breathe, which may cause partial arousal to a lighter state of sleep. The result is fragmented sleep, and, more importantly, cardiovascular disease and other diseases. Conventional therapy for OSA is delivery of continuous positive airway pressure (CPAP) from a pressure generator unit, delivered via a mask worn on the face, thereby, delivering positive pressure to the airway to keep the airway propped open.

OSA therapy is unique from all other forms of ventilation therapy in that the patient has to use the therapy only during sleep. Use during sleep requires that the therapy and devices be comfortable and un-obtrusive for a successful treatment. CPAP has significant unmet needs in that it is highly obtrusive and uncomfortable, because of which a majority of people with OSA remain untreated.

To address the limitations of CPAP, other therapies and interventions have been attempted. Less conventional therapies to treat OSA include tissue ablation, tissue resection, mandibular advancement appliances, implants, magnets and tissue suction devices. These approaches are all intended to prevent the obstruction of the oropharyngeal airway, however, each has disadvantages. Ablation and resection do not work because too much airway must be removed or reduced, thus affecting other airway functions, like swallowing and speech. Implants and magnets do not work because the procedures and devices either do not affect enough of the anatomy to prevent obstructions, or affect too much of the anatomy and adversely affect other airway functions. Suction devices and oral appliances do not work because of user unfriendliness.

Needs exist for approaches that prevent obstruction in a safe and effective manner, while at the same time preserving function of the oro-pharyngeal airway and avoiding any adverse side effects. Needs also exist for methods and apparatus that are less-obtrusive and more comfortable.

Other ventilation-based therapies using catheters or cannula have been described in the prior art. Jacobs ("Transtracheal Catheter Ventilation: Clinical Experience in 36 Patients"; Chest 1974; 65; 36-40) describes ventilating non-spontaneously breathing patients with a transtracheal catheter. McGinley ("A nasal cannula can be used to treat obstructive sleep apnea"; Am J Respir Crit Care Med. 2007 Jul. 15; 176(2):194-200) describes nocturnal treatment of OSA by nasal delivery of oxygen using modified oxygen therapy nasal prongs. Christopher ("Oxygen Therapy Using Pulse and Continuous Flow With a Transtracheal Catheter and a Nasal Cannula"; Chest 1994; 106:854-860) describes treating oxygen dependent patients using a transtracheal catheter for synchronizing the delivery of oxygen therapy to conserve oxygen. Breitenbücher ("Transtracheal oxygen therapy in obstructive sleep apnea syndrome"; Schweiz Med Wochenschr. 1989 Nov. 18; 119(46):1638-41) describes nocturnal treatment of OSA using a transtracheal cannula for continuous flow of gas. Christopher (U.S. Patent Publication No. 2005/0121038) describes a nasal catheter advanced toward the pharynx to directly ventilate the pharynx. Christopher (U.S. Pat. No. 5,954,050) describes a diagnostic transtracheal catheter equipped with respiration sensors used for diagnosing sleep apnea while providing continuous flow oxygen therapy.

While these catheter-based approaches have had some measure of clinical success, they are not effective enough to be embraced as mainstream therapies. The nasal cannula-based approaches tend to be effective with snoring or light OSA, but not moderate or severe OSA, because of the limited pressure it can create at the oropharynx. The transtracheal approaches tend not to have the fidelity and control system intelligence to make the therapies effective over a range of patient and clinical conditions, and, also, do not direct ventilation gas in the most optimal manner.

Needs exist for more effective ways to prevent or treat sleep apnea using catheter ventilation based systems and methods that address the aforementioned shortcomings.

SUMMARY OF THE INVENTION

The current invention is an improvement over existing sleep apnea ventilation therapies. The present invention prevents obstruction of the airway, or alternatively ventilates the lung during an obstruction, with a catheter-based system that is less obtrusive than CPAP, thereby improving compliance and efficacy of the therapy.

In addition, the invention provides improved prediction of the onset of an apneic episode so that the therapy can intervene in a more precise, intelligent and more tolerant manner for the patient. Embodiments of the present invention may include one or more of the following features: (1) catheter-based synchronized ventilation of the lung and/or oropharyngeal airway; (2) catheter-based pressurization of the oropharyngeal airway to prevent or reverse airway obstruction; (3) retrograde ventilation of the oropharyngeal airway; (4) using breathing effort and breathing sensors for apnea prediction and detection and for regulating the therapeutic parameters.

Embodiments of the present invention may include an apparatus for treating sleep apnea having a ventilator for delivering ventilation gas; a control system for the ventilator; a transtracheal ventilation catheter for insertion into a trachea; a distal tip on the transtracheal ventilation catheter; one or more sensors for detecting a breathing cycle; a ventilation gas delivery circuit connecting the ventilator to the transtracheal ventilation catheter; wherein the control system operates the ventilator such that ventilation gas is delivered in synchrony with the breathing cycle; and wherein the distal tip delivers the ventilation gas in a direction selected from the group consisting of superiorly from the transtracheal ventilation catheter towards an upper airway, inferiorly from the transtracheal ventilation catheter towards a lung, and combinations thereof.

The control system may operate the ventilator such that ventilation gas is delivered in a manner selected from the group consisting of during an inspiration phase of the breathing cycle, during an expiration phase of the breathing cycle, during both an inspiration phase and an expiration phase of the breathing cycle, continuously during the breathing cycle, cyclically during the breathing cycle, with a flow amplitude that increases over time, with flow rates adjusted by the control system in response to measurements from the one or more sensors, and combinations thereof. The ventilation gas may be delivered at a low flow rate and a high pressure, or at a high frequency. The ventilation gas may be delivered as a jet. The ventilation gas may be delivered in a manner selected from the group consisting of preemptively to prevent or minimize an obstruction or apneic event, while an obstruction or apneic event is developing, in reaction to an obstruction or apneic event, and combinations thereof.

The one or more sensors may be coupled to the transtracheal ventilation catheter, or external to the trachea. The one or more sensors may be one or more airflow sensors in the trachea and one or more pressure sensors in the trachea. Signals from the one or more airflow sensors and signals from the one or more pressure sensors may be combined by the control system to activate the ventilator. The one or more sensors may be a first sensor for measuring actual respiration air movement and a second sensor for measuring direct or indirect respiratory muscle effort, and wherein the control system processes signals from the first sensor and the second sensor to distinguish conditions selected from the group consisting of light breathing, an obstruction, a reduced respiratory drive, and combinations thereof, wherein the control system activates the ventilator to deliver ventilation gas if the first sensor measures a signal that is abnormally low in amplitude and the second sensor simultaneously measures a signal that is abnormally high in amplitude.

The apparatus may include a humidifier. The ventilation catheter may be inserted through a stoma guide. The distal tip may curve superiorly towards the upper airway within the trachea. The transtracheal ventilation catheter include multiple lumens with a function selected from the group consisting of delivering gas toward the lung, delivering gas toward the upper airway and away from the lung, monitoring pressure of the trachea, containing breath sensor wiring, or combinations thereof. The distal tip may include two ventilation gas exit ports, wherein a first gas exit port directs ventilation gas toward the lung and a second gas exit port directs gas superiorly away from the lung toward the upper airway. The distal tip may include a bifurcation, wherein a first part of the bifurcation is curved or angled inferiorly toward the lung and a second part of the bifurcation is curved or angled superiorly away from the lung toward the upper airway. The ventilation apparatus may operate in a first mode during daytime use for respiratory insufficiency using a first set of parameters and in a second mode during nocturnal used during sleep using a second set of parameters.

Embodiments of the present invention may include a method of treating sleep apnea including inserting a transtracheal ventilation catheter with a distal tip into a trachea; measuring a breathing cycle with one or more sensors; controlling a ventilator with a control system based upon signals from the one or more sensors; delivering ventilation gas from the ventilator to the transtracheal ventilation catheter through a ventilation gas delivery circuit in synchrony with the breathing cycle; and wherein the distal tip of the transtracheal ventilation catheter directs the ventilation gas in a direction selected from the group consisting of superiorly from the transtracheal ventilation catheter towards an upper airway, inferiorly from the transtracheal ventilation catheter towards a lung, and combinations thereof.

Embodiments of the present invention may include a ventilation apparatus for treating sleep apnea including a ventilator for delivering ventilation gas; a control system for the ventilator; a trans-oral ventilation catheter for insertion into an oral cavity; a distal tip on the trans-oral ventilation catheter; one or more first sensors; one or more second sensors; wherein signals from the one or more first sensors and the one or more second sensors are combined to determine a breathing cycle; a ventilation gas delivery circuit connecting the ventilator to the trans-oral ventilation catheter; wherein the control system operates the ventilator such that ventilation gas is delivered in synchrony with the breathing cycle; and wherein the distal tip delivers the ventilation gas in a direction inferiorly from the trans-oral ventilation catheter towards a lung.

Embodiments of the present invention may include a method of treating sleep apnea including inserting a trans-oral ventilation catheter with a distal tip into an oral cavity; measuring a breathing cycle with one or more first sensors and one or more second sensors; controlling a ventilator with a control system based upon signals from the one or more first sensors and the one or more second sensors; delivering ventilation gas from the ventilator to the trans-oral ventilation catheter through a ventilation gas delivery circuit in synchrony with the breathing cycle; and wherein the distal tip of the trans-oral ventilation catheter directs the ventilation gas in a direction inferiorly from the trans-oral ventilation catheter towards a lung.

Embodiments of the present invention may include a ventilation apparatus for treating sleep apnea including a ventilator for delivering ventilation gas; a control system for the ventilator; a trans-nasal ventilation catheter for insertion into an nasal cavity; a distal tip on the nasal-oral ventilation catheter; one or more first sensors; one or more second sensors; wherein signals from the one or more first sensors and the one or more second sensors are combined to determine a breathing cycle; a ventilation gas delivery circuit connecting the ventilator to the trans-nasal ventilation catheter; wherein the control system operates the ventilator such that ventilation gas is delivered in synchrony with the breathing cycle; and wherein the distal tip delivers the ventilation gas in a direction inferiorly from the trans-nasal ventilation catheter towards a lung.

Embodiments of the present invention may include a method of treating sleep apnea including inserting a trans-nasal ventilation catheter with a distal tip into an nasal cavity; measuring a breathing cycle with one or more first sensors and one or more second sensors; controlling a ventilator with a control system based upon signals from the one or more first sensors and the one or more second sensors; delivering ventilation gas from the ventilator to the trans-nasal ventilation catheter through a ventilation gas delivery circuit in synchrony with the breathing cycle; and wherein the distal tip of the trans-nasal ventilation catheter directs the ventilation gas in a direction inferiorly from the trans-oral ventilation catheter towards a lung.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE FIGURES

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 16b describes the retrograde catheter of FIG. 16a.

LIST OF REFERENCE SYMBOLS USED IN THE FIGURES

Figure 1:
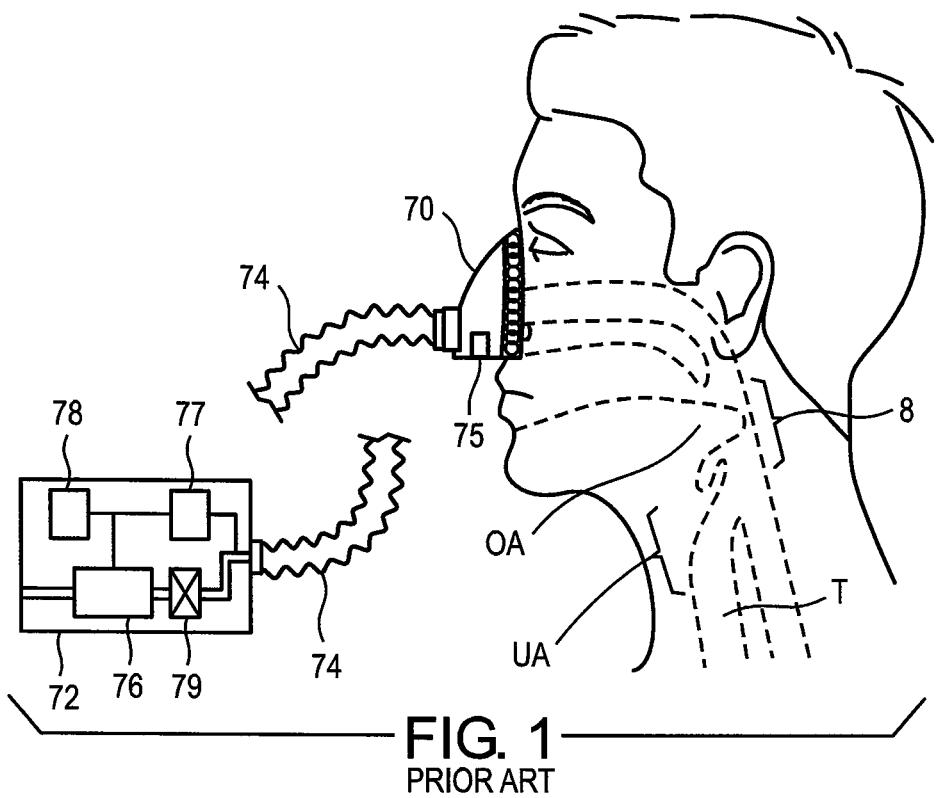
FIG. 1 is a diagram showing prior art for treating OSA with CPAP therapy.

L lung
T trachea
V ventilator
VO ventilator gas output
OA oropharyngeal airway
UA upper airway
IQ inspiratory flow
EQ expiratory flow
IP inspiratory pressure
EP expiratory pressure
A ventilation flow
R retrograde gas flow
t time
Q airway flow signal
P airway pressure signal
I inferior side
S superior side
5 ventilation catheter neck flange
7 connection
8 oropharyngeal obstruction
10 transtracheal catheter
10' transtracheal catheter with retrograde flow
10" transtracheal catheter with normal and retrograde flow
11 inferior gas exit port
12 stoma
15 superior gas exit port
20 ventilation gas delivery circuit
20' gas delivery circuit
20" gas delivery circuit
32 normal airflow signal
34 reduced airflow signal
38 increased breath effort signal
40 ventilator flow/volume synchronized with inspiration
42 continuous flow
43 increasing ventilator continuous flow signal
44 ventilator flow/volume at rate based on past breath rate history
45 ventilator volume in retrograde direction
46 ventilator flow/volume synchronized with exhalation
47 cyclical volume delivery
48 obstructed breath signal
49 retrograde high frequency volume delivery
50 retrograde ramping continuously increasing flow delivery
60 proximal end connector
61 gas delivery channel connector
62 respiration sensor connector
63 pressure monitoring lumen connector
64 main channel
65 secondary lumen
66 delivery circuit pneumatic sensing lumen
67 combined connector
68 detachable connector
70 CPAP ventilation mask
72 CPAP ventilator
74 CPAP single limb breathing circuit
75 mask vent port
76 flow generator
77 pressure sensor
78 control system
79 control valve
80 intra-tracheal airflow sensor
82 sensor wires
84 sensor wire lumen
85 tubing
86 pressure sensing port
88 pressure sensing lumen
90 catheter distal tip restriction
92 catheter distal tip section
100 retrograde catheter
120 combined retrograde and normal direction ventilation catheter
121 gas delivery channel
123 gas delivery channel
125 combined retrograde and normal direction gas delivery lumen
130 stoma guide
131 stoma guide neck flange
133 stoma guide pedals
135 stoma guide strap
136 stoma guide keyway
160 gas delivery pressure sensor
161 gas delivery mechanism
162 pressure monitoring line
163 gas delivery control system
165 gas delivery control valve
168 humidifier
169 patient spontaneous respiration sensor
170 dual control valve
171 lung directed valve gas output
172 retrograde directed valve gas output
180 dual connector
181 lung directed gas flow connector
182 retrograde directed gas flow connector
200 trans-nasal catheter
220 trans-oral catheter
222 lingual flange
224 buccal flange
225 ventilation circuit neck strap
230 oral breath sensor
232 intra-oral breath sensor
234 nasal breath sensor
235 flange
236 intra-nasal breath sensor
300 external airflow sensor
302 external airflow sensor securing tape or head strap
304 external airflow sensor wireless signal transmission 306 external airflow sensor signal wire
308 ventilator airflow sensor signal receiver
310 wireless external breath effort sensor
312 external breath effort sensor
314 external breath effort sensor wire

DETAILED DESCRIPTION OF THE PREFERRED EMBODIMENTS

FIG. 1 illustrates a continuous positive airway pressure (CPAP) system, which is the state-of-the-art therapy for treating obstructive sleep apnea (OSA). When an oropharyngeal obstruction 8 occurs, the patient can no longer breathe spontaneously through their mouth or nose. The oropharyngeal obstruction 8 may occur above a trachea (T) and an upper airway (UA). For treatment, CPAP is delivered with a CPAP ventilator 72, a CPAP single limb breathing circuit 74, and a CPAP ventilation mask 70 with one or more mask vent ports 75. Pressurized gas is delivered to the upper airway (UA) to prevent the oropharyngeal airway (OA) from obstructing. All of the gas being received by the lungs of the patient is received from the CPAP ventilator 72 because the CPAP system is a closed system. The pressurized gas is created by a pressure or flow generator 76, typically a blower, in the CPAP ventilator 72. During exhalation, the patient exhales through the one or more mask vent ports 75 and back through the CPAP single limb breathing circuit 74. The CPAP ventilator 72 also includes a pressure sensor 77, a control system 78 and a control valve 79 to control CPAP ventilator 72. CPAP therapy is unpopular due to the invasiveness of a closed system, the obtrusiveness of wearing the mask, the unnatural feeling of positive pressure delivery and exhalation, and added artificial heated humidification (not shown).

FIGS. 2-27 illustrate various embodiments of the present invention.

FIG. 2 illustrates an embodiment of the invention in which a minimally invasive open airway transtracheal ventilation system may be used to prevent, minimize or reverse an upper airway obstruction, or provide ventilation while there is an obstruction. The present invention may include a ventilator (V) with a gas delivery mechanism 161, a gas delivery control system 163, a gas delivery control valve 165, a gas delivery pressure sensor 160, and a patient spontaneous respiration sensor 169.

The gas delivery mechanism 161 can include a piston, blower, pump, gas accumulator, pressurized gas source or liquid oxygen source, or can simply be an input from an external gas source. The output of the gas delivery mechanism 161 may be controlled by a gas delivery control valve 165 or a proportional valve. The gas delivery control system 163 may receive information from either or both of a respiration sensor internal to the ventilator, or a respiration sensor external to the ventilator, for example, an intra-tracheal airway sensor 80, as shown, or a pressure sensing lumen described later. The gas delivery control system 163 may receive input from a gas delivery pressure sensor 160 and/or respiration sensor or other sensors. The gas delivery control system 163 may control the ventilation gas delivery mechanism 161 and the gas delivery control valve 165 to provide a desired therapeutic output and effect on the patient.

The present invention also includes a ventilation gas delivery circuit 20, and a transtracheal catheter 10, which may include the respiration sensor such as, for example, the intra-tracheal airflow sensor 80. Ventilation gas can be air, oxygen or blended air and oxygen. Humidity can be fed into the gas delivery circuit from an optional humidifier 168.

One or more respiration sensors, such as the intra-tracheal airflow sensor 80, and the gas delivery control system 165 may be critical in monitoring a patient's breathing, predicting or detecting of the presence of obstructions or apneic episodes, and synchronizing the ventilator (V) output with the patient's respiration. The one or more respiration sensors can measure airflow in the trachea (T), measure tracheal pressure, or both. When measuring airflow, the airflow signal reduces during an upper airway obstruction because the obstruction reduces the actual airflow through the trachea. When measuring pressure, the tracheal pressure signal may increase during an obstruction because of the increased pressure drop occurring in the trachea. As will be described throughout, a dual sensing approach may be preferred because one sensor is used for measuring actual respiration while the other sensor is used for measuring respiration effort. The combination of the two measurements may allow the system to distinguish between apnea and light breathing or between OSA and CSA. The two measurement system may provide more predictive information than a single sensor. For example, actual respiration can be sensed via sensing airflow in the trachea, and respiration effort can be sensed via measuring tracheal pressure or chest movement.

The one or more intra-tracheal airflow sensors 80 can be, for example, one or more thermal sensors detecting direction of airflow in the trachea T, pressure sensors such as strain gage sensors, a pressure monitoring lumen terminating in a pressure monitoring port, airflow sensors such as a heated wire anemometer, an accelerometer sensor, or a gas composition sensor such as a $CO_2$ sensor. The one or more intra-tracheal airflow sensors 80 can optionally be in contact with tissue. If the one or more intra-tracheal airflow sensors 80 are in contact with tissue, they may be, for example, pulse oximetry sensors, strain gauge sensors, muscle activity sensors or neurological sensors. The one or more intra-tracheal airflow sensors 80 can also optionally be external to the transtracheal catheter (See, for example, element 300 in FIG. 26). In this case, the one or more intra-tracheal airflow sensors 80 may be nose or mouth thermal or airflow sensors or chest impedance sensors, such as RespiTrace sensors.

The transtracheal catheter 10 may be placed through a stoma 12 in the neck of a patient and into the trachea (T). Optionally, a stoma guide 130 may be placed into the stoma 12, and the transtracheal catheter 10 placed into the stoma guide 130 to allow easier removal and reinsertion of the transtracheal catheter 10, as needed. The stoma guide 130 may typically include one or more flanges or pedals on an outside proximal end and, optionally, one or more flanges or pedals on the inside distal end to secure the stoma guide 130 in place in the neck and stoma 12. The transtracheal catheter 10 may typically include a neck flange 5 to secure the transtracheal catheter 10 to the stoma guide 130 or neck, and a connection 7 to the gas delivery circuit 20. Ventilation flow may exit the transtracheal catheter 10 at a distal tip gas exit port 11. The gas exit port 11 may direct ventilation flow (A) toward a lung (L).

A patient may generally have inspiratory flow (IQ) and expiratory flow (EQ). In addition to inspiratory flow (IQ) and expiratory flow (EQ), the ventilation flow (A) of the present invention may be described as augmentation or augmented ventilation; however, this is exemplary only and the ventilation may include higher levels of volume and may be considered simply ventilation. Ventilation gas delivery can be: (1) a volume level that augments the patient's spontaneous tidal volume, such as 50 ml to 200 ml; (2) a substantial amount of the patient's required at-rest tidal volume, such as 150 ml to 300 ml; (3) a full at rest tidal volume, such as 350 ml to 600 ml; (4) a volume in excess of the patient's normal at rest volume, such as 400 ml to 800 ml; or (5) another suitable volume.

Figure 2A:
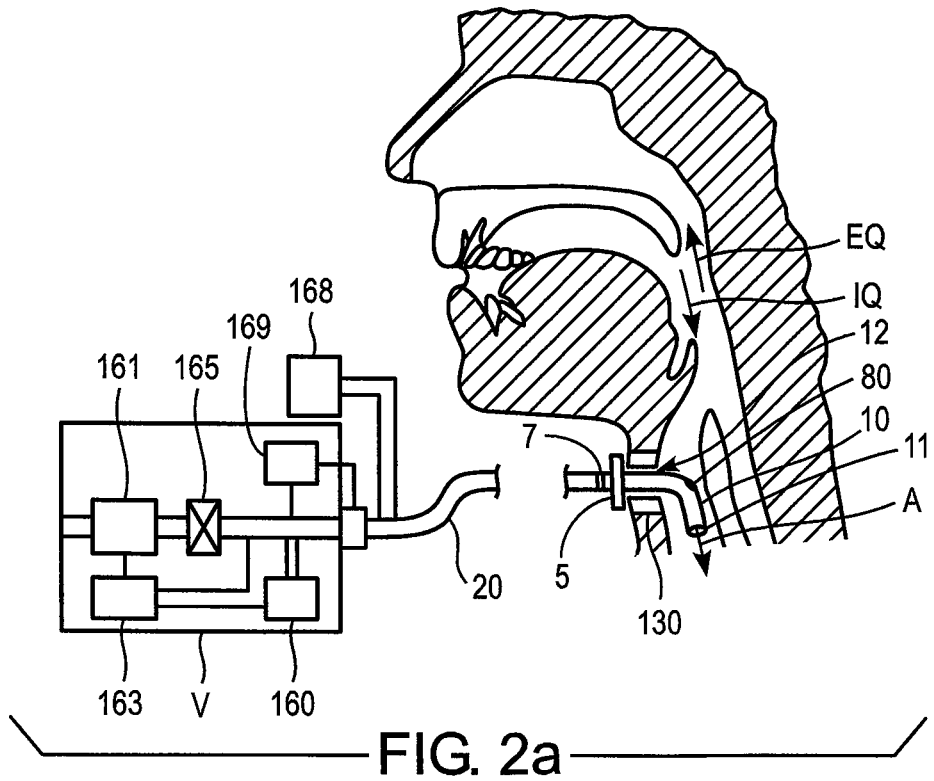
FIG. 2a is a diagram showing a transtracheal ventilation method and apparatus for treating OSA, including a transtracheal ventilation catheter, gas delivery circuit, breath sensing, ventilator, and ventilation control system.
Figure 2B:
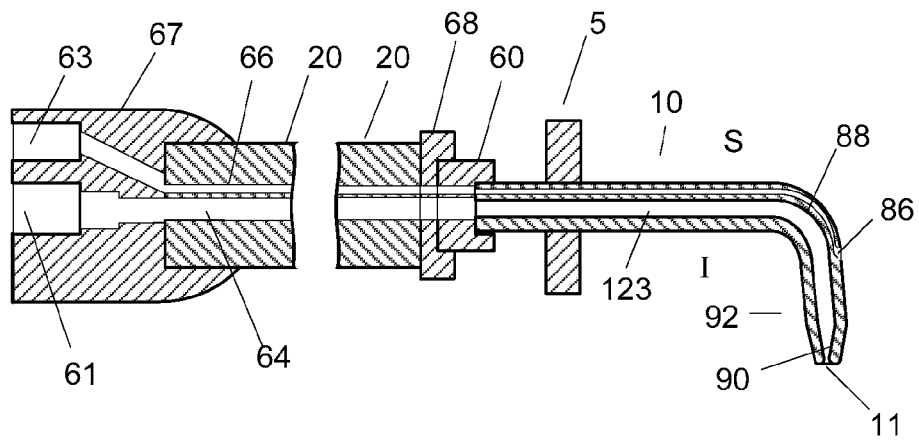
FIG. 2b describes the ventilation catheter and gas delivery circuit of FIG. 2a in more detail, in which the breath sensing is performed with a pressure sensing lumen.
Figure 2C:
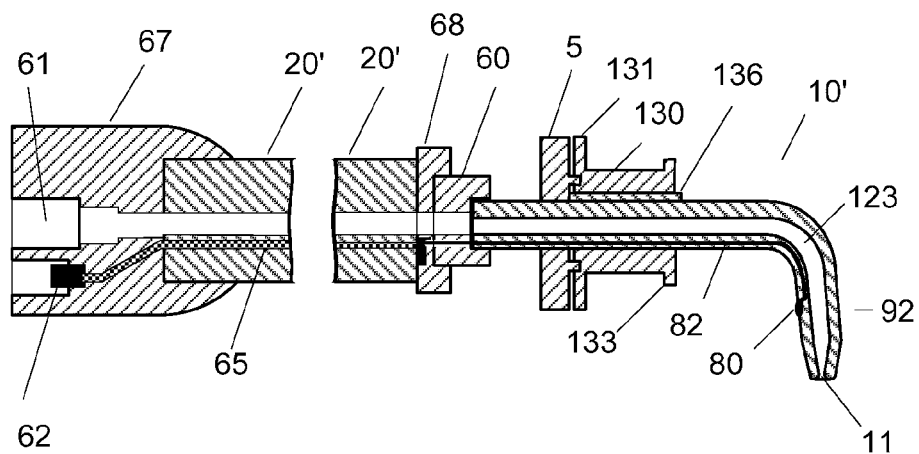
FIG. 2c describes an alternative to FIG. 2b in which the sensing is performed with an active intratracheal sensor.
Figure 2D:
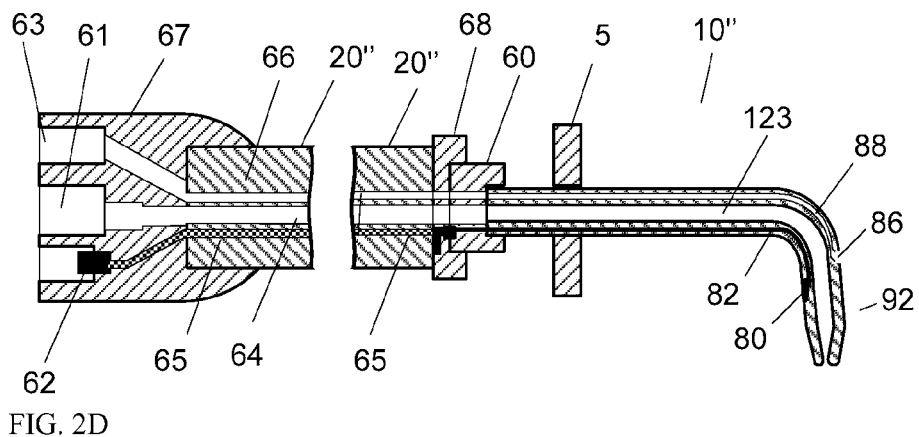
FIG. 2d describes an alternative to FIG. 2c in which the sensing is performed with both an active intratracheal sensor and a pressure sensing lumen.

The transtracheal catheter 10 and the ventilation gas delivery circuit 20 is described in more detail in FIGS. 2b-2d. In FIG. 2b, the ventilation gas delivery circuit 20 may include a proximal end connector 60, which further includes a gas delivery channel connector 61 and a respiration sensor connector 62. The ventilation gas delivery circuit 20 may include a main channel 64 for gas delivery, and a secondary lumen 65 for conducting a respiration sensor signal. A pressure monitoring lumen connector 63 may be located in a combined connector 67 and in communication with a delivery circuit pneumatic sensing lumen 67. The ventilation gas delivery circuit 20 may be connected to the transtracheal catheter 10 with a detachable connector 68 near the patient or, alternatively, a connector permanently attached to the transtracheal catheter 10. The transtracheal catheter 10 may include a ventilation catheter neck flange 5 if the transtracheal catheter 10 is inserted directly into the patient's stoma 12. Using stoma guides 130 between the transtracheal catheter 10 and stoma 12, however, may also be possible as will be explained later.

The transtracheal catheter 10 may include a gas delivery channel 123, a pressure sensing lumen 88 and a pressure sensing port 86. The transtracheal catheter may be curved so that a catheter distal tip section 92 is parallel with the axis of the trachea (T), typically curved in a 90-110 degree bend. The catheter distal tip section 92 may include a catheter distal tip restriction 90 at an exit point to increase the exit velocity of the ventilation flow (A), if a venturi is the desired effect. The pressure sensing lumen 88 can optionally be flushed to maintain patency with a flushing mechanism typically included in the ventilator (V). Other types of sensor designs are described in subsequent descriptions and may be used in any of the embodiments of the present invention. The pressure sensing port 86 may be positioned parallel to the trachea's longitudinal axis to reduce directionality-related artifacts. Other possible positions and orientations of the pressure sensing port 86 are described below.

Optionally, the pressure sensing port 86 can be positioned orthogonal to the trachea's longitudinal axis, such as on the top or superior surface (S) of the transtracheal catheter 10. A superior orientation may provide a sensitive reading for inspired airflow and a less sensitive reading during expired airflow, perhaps due to venturi effects. If accuracy during inspiration is deemed more critical, then the pressure sensing port 86 can be oriented on the superior surface. If, however, accuracy during exhalation is deemed more critical, then the pressure sensing port 86 can be oriented on the inferior surface (I) of the transtracheal catheter 10. Alternatively, the transtracheal catheter 10 can be configured with two pressure sensing ports 86 connected to the pressure sensing lumen 88 and, therefore, the signals seen at the two pressure sensing ports 86 may be combined into one average signal. Alternatively, the transtracheal catheter 10 can be configured with two pressure sensing ports 86, one on the inferior surface (I) and one on the superior surface (S) with each pressure sensing port 86 connected to a dedicated pressure sensing lumen 88 connected to two dedicated pressure transducers in the ventilator (V). This configuration may provide high accuracy for both exhalation (the inferior sensing port) and inspiration (the superior sensing port). This configuration can also be used to determine flow.

FIG. 2c illustrates an alternative transtracheal catheter with retrograde flow 10' and gas delivery circuit 20'. In this example, the transtracheal catheter with retrograde flow 10' may include an intra-tracheal airflow sensor 80. The intra-tracheal airflow sensor 80 communicates with the ventilator (V) via one or more sensor wires 82 placed in a sensor wire lumen 84 in the transtracheal catheter with retrograde flow 10' and tubing 85 in the gas delivery circuit 20'. In FIG. 2c, the intra-tracheal airflow sensor 80 may include an active element such as, but not limited to, a thermal, mechanical, electrical, chemical, or optical element. Also in FIG. 2c, a stoma guide 130 may be placed between the transtracheal catheter with retrograde flow 10' and the stoma 12. The stoma guide 130 may include a stoma guide neck flange 131 or pedals on the surface of the neck and a stoma guide strap 135 to secure the stoma guide 130 in place. The stoma guide 130 may optionally include a flange or one or more stoma guide pedals 133 on the inside of the trachea (T) to prevent dislodgement. The stoma guide 130 can include a stoma guide keyway 136 to mate with a mating feature on the transtracheal catheter with retrograde flow 10' to rotationally orient the alternative transtracheal catheter with retrograde flow 10' correctly. The alternative transtracheal catheter with retrograde flow 10' may be connected to the stoma guide 130 with a ventilation catheter neck flange 5.

FIG. 2d illustrates an alternative catheter design in which a transtracheal catheter with normal and retrograde flow 10" includes both an active intra-tracheal airflow sensor 80 with a pressure sensing port 86 and a pressure sensing lumen 88. In this case, for example, the intra-tracheal airflow sensor 80 can be used for measuring one respiration parameter, such as air flow or gas composition, while the pressure sensing port 86 can be used to measure a different respiration parameter, such as tracheal pressure or respiratory effort. A gas delivery circuit 20" may have necessary connections for connecting to the ventilator (V). Connections may include the gas delivery channel connector 61, a pneumatic pressure sensing connector 63, and the respiration sensor connector 62.

The transtracheal catheters 10, 10', 10" of FIGS. 2a-2d may include one or more curves to position the distal tip in the tracheal lumen in a non-irritating fashion. Irritation may be minimized by reducing or eliminating contact of the transtracheal catheters with the tracheal wall. Alternatively, irritation may be minimized by contacting the transtracheal catheters with the tracheal wall but reducing or eliminating movement against the tracheal wall. Reduction of irritation may be best accomplished if there is no moveable contact between the transtracheal catheters and tracheal wall, and, most preferably, if there is no contact between the transtracheal catheters and a tracheal wall, especially the posterior tracheal wall. Ideally, the transtracheal catheters are designed with a curve of approximately 90°-120° in the inserted section to curve the catheter distal tip section into alignment with the axis of the trachea (T), and to direct the catheter tip toward the main stem bronchii.

The length of the transtracheal catheters 10, 10', 10" may extend distal to the skin for a distance of approximately 10-200 mm, preferably approximately 20-100 mm; and an outer diameter (OD) of the ventilation catheters may be approximately 3-10 mm, preferably approximately 4-6 mm; and an inner diameter of the ventilation catheters 10 may be approximately 0.75-3 mm, preferably approximately 1-2 mm.

The transtracheal catheters 10, 10', 10" may have one gas delivery channel 123. The transtracheal catheters may have a secondary lumen 84 for sensor wires 82 and/or for a pressure sensing lumen 88. The transtracheal catheters 10, 10', 10" may be molded, extruded or formed from thermoplastic material such as PVC, nylon-based materials, or PVC-urethane blends, or alternatively, may be molded using an elastomeric material, such as silicone or urethane. The transtracheal catheter material may typically be approximately 30-90 Shore A durometer. A transtracheal catheter tip may be rounded to provide an atraumatic surface. The ID at the distal tip is optionally restricted to approximately 10-75%, preferably 40-60%, to increase gas flow exit speed, which is desirable when a venturi effect is desired.

The gas delivery circuits 20, 20', 20" lengths may be approximately 20-100 inches, preferably approximately 30-40 inches, with an OD of approximately 6-16 mm, preferably approximately 6-10 mm, and an ID of approximately 2-10 mm, preferably approximately 3-5 mm. The gas delivery circuits 20, 20', 20" may be very lightweight, extruded thermoplastic material such as polypropylene or polyethylene.

Figure 3:
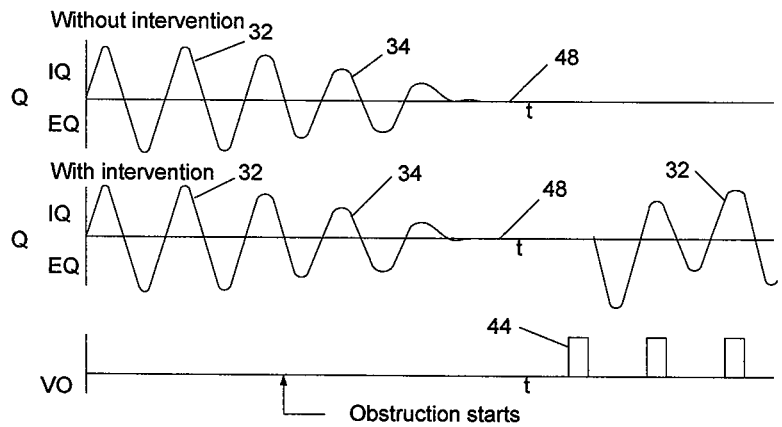
FIG. 3 is a graph showing when the transtracheal ventilation is activated in reaction to an obstruction or apneic event.
Figure 4:
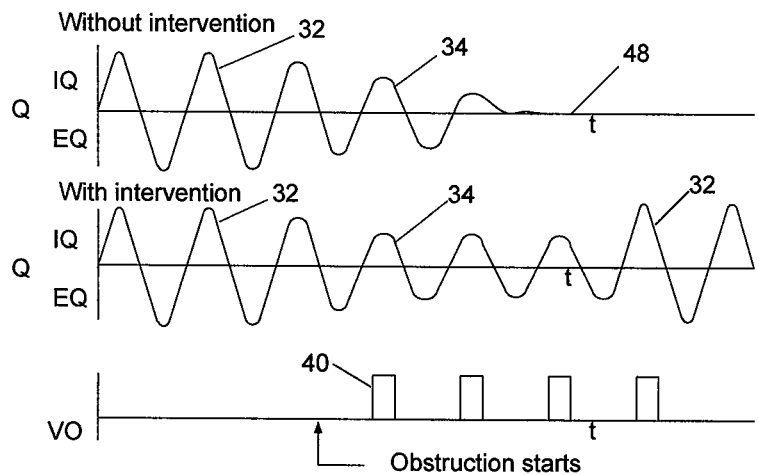
FIG. 4 is a graph showing when the transtracheal ventilation is activated in anticipation of an obstruction or apneic event.
Figure 5:
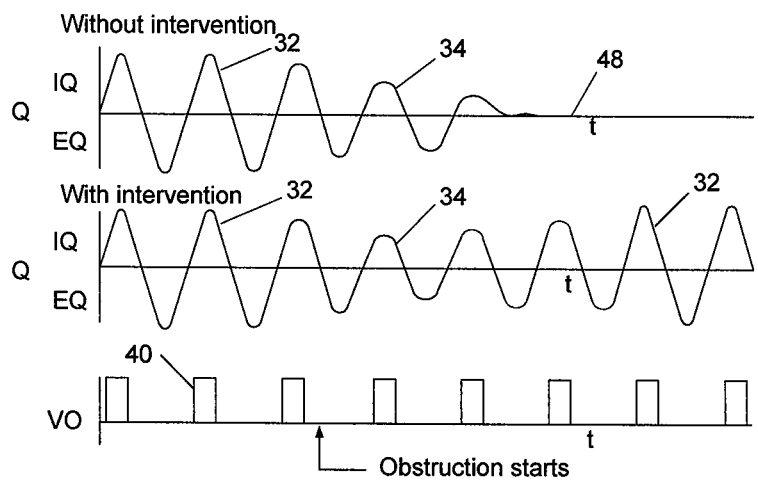
FIG. 5 is a graph showing when the transtracheal ventilation is activated proactively to prevent an obstruction or apneic event.
Figure 27:
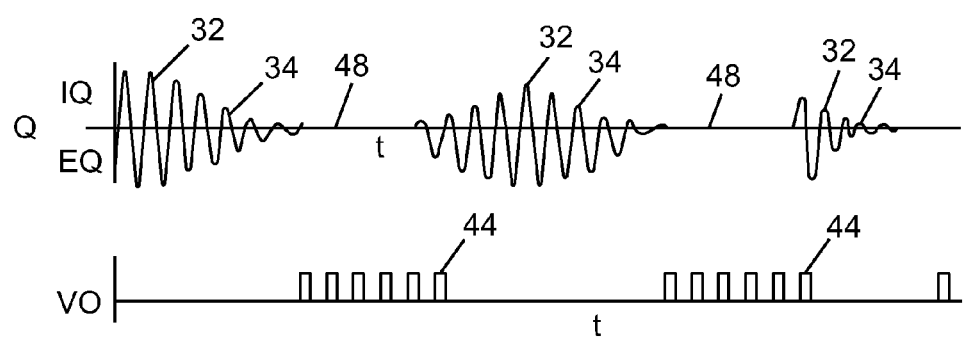
FIG. 27 is a graph showing administering the transtracheal ventilation method, over a period of time.

FIGS. 3-5 and 27 graphically illustrate the respiration sensing, ventilation control and gas delivery aspects of the embodiment shown in FIG. 2a. This series of graphs show alternative gas delivery methods of the present invention: FIG. 3 shows transtracheal ventilation in response to an apneic event; FIG. 4 shows transtracheal ventilation in response to the beginning or precursor of an apneic event to prevent the apneic event from worsening; FIG. 5 shows transtracheal ventilation proactively to preempt an apneic event; and FIG. 27 shows transtracheal ventilation activated during periods of apnea or airway obstruction and then deactivated when breathing is restored. In this series of graphs, t is the time axis, Q is the airway flow signal, IQ is the inspiratory flow signal, EQ is the expiratory flow signal, VO is the ventilator output, 32 is the normal breathing flow curve, 34 is a breathing flow curve when the airway is partially obstructed, and 48 is an obstructed airflow signal.

FIG. 3 graphically shows transtracheal ventilation activated in reaction to an obstruction or apneic event. The one or more intra-tracheal airflow sensors 80 may detect a shift in tracheal airflow from a normal airflow signal 32 to a reduced airflow signal 34. As seen in the graph labeled "with intervention", immediately after the reduced airflow signal 34 is detected by the respiration sensor or, alternatively, after some desired delay, the gas delivery control system 163 may command the ventilator (V) to deliver ventilation flow/volume at a rate based on past breath rate history 44. The ventilation flow A may open the obstruction and restore respiration as seen in the graph labeled "with intervention" and restore ventilation to and at the lung (L). For contrast, the graph labeled "without intervention" shows the respiration signal eventually going to no airflow signal 48, thus indicating a substantially complete obstruction. In the example shown, during the period of partial or complete obstruction, the flow signal in the trachea (T) is not strong enough for the one or more intra-tracheal airflow sensors 80 to detect respiration, and ventilation flow A is delivered from the ventilator (V) at a rate based on previous spontaneous breath rate history 44 of the patient. Alternatively, the ventilation flow (A) can be delivered from the ventilator (V) at a pre-determined back-up rate.

In a variation to FIG. 3, in which transtracheal ventilation is activated upon detection of an obstruction, FIG. 4 graphically shows transtracheal ventilation activated in anticipation or prediction of an obstruction or apneic event. The one or more intra-tracheal airflow sensors 80 may detect a shift in tracheal airflow from a normal airflow signal 32 to a reduced airflow signal 34. Either immediately or after some desired delay, the control unit 159 may command the ventilator (V) to deliver ventilation flow (A) synchronized with inspiration 40. Alternatively, the ventilation flow (A) can be delivered at a pre-determined back-up rate.

FIG. 5 graphically shows transtracheal ventilation activated proactively to prevent an obstruction or apneic event. The one or more intra-tracheal airflow sensors 80 may detect a shift in tracheal airflow from a normal airflow signal 32 to a reduced airflow signal 34. The control unit 159 may command the ventilator V to deliver ventilation flow (A) synchronized with inspiration 40. Alternatively, the ventilation flow (A) can be delivered at a pre-determined back-up rate.

In the embodiments of FIGS. 3-5, activation of transtracheal ventilation prior to an obstruction can have the unwanted side effect of creating additional negative pressure in the upper airway due to the venturi effect of the gas exiting the catheter. This increased negative pressure can contribute to airway collapse. To prevent or minimize this side effect, the ventilation gas parameters may be constantly adjusted to an appropriate pressure, speed, and volume. During proactive transtracheal ventilation, if the respiration sensors detect an onset of upper airway closure, the ventilation parameters may be adjusted. If, however, obstruction occurs partly because of proactive transtracheal ventilation, then the mechanism of action described in FIG. 3 may prevail and the treatment will be successful. Additional embodiments are presented to prevent having to compensate for an unwanted side effect.

Optionally, high frequency low volume ventilation can be delivered by the ventilator (V) and transtracheal catheters 10, 10', 10" where very low volumes of gas are delivered at very fast frequencies, such as approximately 5-100 ml at approximately 12-120 cycles per minute, or preferably approximately 10-20 ml at approximately 30-60 cycles per minute. In this manner, substantial minute volumes can be delivered to the lung (L) without creating a substantial negative pressure at the oropharyngeal airway (OA).

FIG. 27 graphically shows that transtracheal ventilation can be activated during periods of apnea or airway obstruction, where the ventilation flow (A) is activated and then is deactivated when breathing is restored. The ventilation flow (A) may be delivered cyclically when activated. The one or more intra-tracheal airflow sensors 80 may detect a shift in tracheal airflow from a normal airflow signal 32 to a reduced airflow signal 34. The control unit 159 may command the ventilator (V) to deliver augmentation flow (A) at a rate based on past breath rate history 44 during an obstructed breath signal 48. Alternatively, the ventilation augmentation (A) can be delivered at a pre-determined back-up rate.

The one or more intra-tracheal airflow sensors 80 may operate according to the following principles. During a partial obstruction, gas flow in the trachea (T) is reduced due to the obstruction. The tracheal pressure signal may typically increase because of the increased pressure drop required to move air across the partial obstruction. During a complete obstruction, the gas flow in the trachea consists of back and forth movement of air that is already in the trachea (T) and the lung (L), and the tracheal pressure signal registers a higher amplitude because the trachea (T) and the lung (L) are closed off from ambient. While tracheal flow is shown in the graphs, that is exemplary, and with the above explanation, the present invention also includes using tracheal pressure for a control system input as well as tracheal airflow, or both pressure and airflow. Therefore, during a partial or complete obstruction, the pressure based respiration sensor may be particularly effective in detecting the obstruction because of measuring the pressure amplitude increase that may occur due to the higher pressure drop across the obstructed ore more resistive airway.

Using both pressure and airflow sensors may be desired because the information can be crosschecked against each other, for example, a reduced airflow signal plus a increased pressure signal may correspond to an obstruction event. Further, other respiration sensor types described previously, and their respective signal response to an obstruction or apneic event, are also included in the present invention. It should be noted that in CSA the lung is not breathing and hence there is no airflow or pressure signal during an apneic event. The pressure sensor or flow sensor or combinations thereof can distinguish between normal breathing and apneic events, for both OSA, CSA, and patients with both OSA and CSA.

The following describes the mechanism of action of the therapy. During a partial or complete obstruction of the upper airway, there is an increase in airway resistance above or superior to a gas delivery exit point on a distal tip of a transtracheal catheter. Therefore, the breathing system is no longer an open airway breathing system; it is now a closed system, or partially opened system. Therefore, the gas being delivered by the ventilator and catheter, has a significantly greater propensity of entering and inflating the lung, rather than escaping out of the mouth. Assuming a normal adult and healthy lung, for example, with a compliance of about 50 ml/cmH$_2$O and lower airway resistance of 5 cmH$_2$O/L/sec, before upper airway obstruction, 30-70% of the ventilation gas flow exiting the catheter may enter the lung and the balance may leak out of the mouth or nose. In contrast, after the airway obstruction, 50-100% of the ventilation gas flow exiting the catheter may enter the lung, depending on the degree of the obstruction. Therefore, during a partial or complete upper airway obstruction, the present invention is particularly effective in ventilating the lung, which is also an episode where lung ventilation is most needed.

It is noted that because of the gas flow delivery from the catheter, a region of transient negative pressure may be generated above the catheter, which induces further collapse of the upper airway tissues and hence increases the obstruction. The transient negative pressure should transition to positive pressure since the lung and trachea are a closed or almost closed system to which gas volume is being added by the ventilator. Nonetheless, the potential negative pressure in the upper airway is an undesirable side effect. However, this side effect can be deemed clinically acceptable since the primary objective, lung ventilation, is accomplished. Also, during the patient's spontaneous exhalation, the gas in the airways is pressurized due to lung and chest recoil, and hence the airway pressure may open the obstruction to permit exhalation out the upper airway and mouth or nose. Nevertheless, to help overcome the problem of ventilation-induced upper airway collapse, exhalation can also be augmented by the invention, as will be described in later embodiments.

In addition to therapeutic parameters described elsewhere, some of the parameters are as follows: Volume delivery can be approximately 10 ml to 200 ml per ventilator cycle depending on the breathing status of the patient. If complete apnea occurs, volume delivery increases to approximately 200 ml to 500 ml per cycle, at a rate of approximately 6-20 cycles per minute. The flow rate of the gas being delivered is typically approximately 6-50 LPM during the actual delivery of the gas, and preferably approximately 10-20 LPM. Timing of the ventilator cycling can be in synch with the patient's breath rate, for example, approximately 6-30 BPM, or if not synchronized or if the patient is apneic, cycling can be approximately 8-20 cycles per minute unless high frequency low volume ventilation is used, which is described subsequently. The drive pressure at the ventilator output for the ventilation is typically approximately 5-60 psi and preferably approximately 8-40, and most preferably approximately 10-15 psi, to create a desired tracheal pressure of approximately 0-5 cmH$_2$O under normal unobstructed conditions during inspiration and up to approximately 20 cmH$_2$O during obstructed conditions.

It should be noted that in the graphical examples provided, the respiration sensor waveform is exemplary only and actual waveforms can take on other characteristics, such as different I:E ratios, breath rates, random behavior, ascending and descending shapes of inspiratory and expiratory curves, and altering amplitudes.

It should also be noted that while ventilation flow (A) is often shown in synchrony with a breath cycle, the breath cycle may not be detectable due to a partial obstruction or apneic event, and, therefore, the ventilation flow (A) is simply applied at a predetermined rate or a predicted rate. It should also be understood that depending on the sensor used, the breath effort may still be detectable even though there is no or very little airflow being inspired from ambient or being exhaled to ambient. However, the movement of air in the trachea (T) in response to the breath effort in some cases, depending on the sensor technology being used, may be enough to register as an inspiratory effort and expiratory effort by the sensor. In fact, in some cases, depending on the sensor used, an obstruction may be accompanied by an increased negative pressure during inspiration, and, while there is reduced airflow in the trachea T because of the obstruction, the breath signal may be stronger. Therefore, in the present invention, the gas delivery control system 163 and algorithms in the gas delivery control system 163 takes all these matters into account while processing the sensor information and deciding whether there is normal or reduced breathing taking place at any given time.

It should also be noted that ventilation gas delivery, when activated, can gradually ramp up so that it is not a sudden increase in amplitude, which could arouse the patient.

The ventilation pressures achieved in the upper airway by the delivery of the ventilation flow (A) may be in the range of approximately 1-20 cmH2O, preferably approximately 2-5 cmH2O when delivered preemptively, and approximately 5-10 cmH2O when delivered in response to a detected obstruction event. The ventilation pressures achieved in the lower airways and lung may be similar to the pressures achieved in the upper airway by the ventilation gas delivery.

As will be described later, ventilation can be delivered in synchrony with inspiration, or in synchrony with exhalation, or both, or can be delivered at a high frequency, a constant flow, in a retrograde direction, and all possible combinations of the above. When synchronized with the patient's inspiratory or expiratory phase, the ventilator (V) may deliver volume in ranges from approximately 40-700 ml per cycle, preferably approximately 75-200 ml, in delivery times of approximately 0.2 to 1.2 seconds, preferably approximately 0.35-0.75 seconds, and with a catheter exit speed of approximately 50-300 m/sec., preferably approximately 150-250 m/sec.

When delivered at a high frequency rates, the ventilator (V) may deliver volume at a rate of approximately 0.25 cycles per second to approximately 4 cycles per second, preferably at a rate of approximately 0.5 to 2 cycles per second, in the range of approximately 10 ml to 100 ml per cycle, preferably approximately 25-75 ml per cycle.

When delivered at a constant flow, the ventilator V may deliver flow at a rate of approximately 0.5 LPM to 10 LPM, preferably approximately 2-6 LPM, and at a catheter exit speed of approximately 50 m/sec to 250 m/sec, preferably approximately 100-200 m/sec.

FIGS. 6-15 graphically describe variations of the transtracheal ventilation parameters used in the present invention, including timing, synchronization, waveform and amplitude alternatives. In this series of graphs, t is the time axis, P is the airway pressure signal, Q is the airway flow signal, IP is the inspiratory pressure, EP is the expiratory pressure, IQ is the inspiratory flow signal, EQ is the expiratory flow signal, VO is the ventilator output, 32 is the normal breathing flow curve, and 34 is a breathing flow curve when the airway is partially obstructed.

Figure 6:
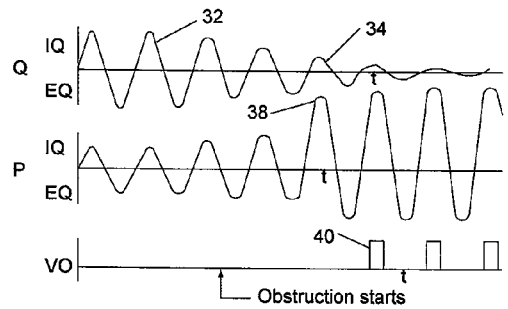
FIG. 6 is a graph showing when the transtracheal ventilation is activated to alleviate an obstruction or apneic event, where the ventilation gas is synchronized with the inspiratory phase of the breath cycle.

FIG. 6 graphically describes an embodiment of the present invention where the transtracheal ventilation is activated to alleviate an obstruction or apneic event and the ventilation gas (A) flow/volume may be synchronized with the inspiration 40 of the breath cycle. A reduced airflow signal 34 is detected by the one or more intra-tracheal airflow sensors 80, however, an increased breath effort signal 38 may also be detected by a redundant pressure signal monitored via a catheter tip based sensor or a pressure sensing lumen 88 in the transtracheal catheter 10 and connected to the ventilator (V) through a channel typically connected to the gas delivery circuit.

Figure 7:
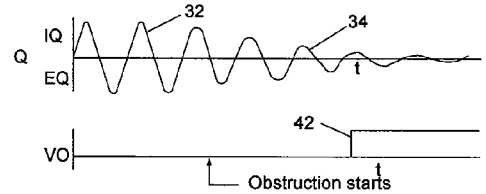
FIG. 7 is a graph showing when the transtracheal ventilation is activated to alleviate an obstruction or apneic event, where the ventilation gas is delivered as a continuous flow.

FIG. 7 graphically describes an embodiment of the present invention where the ventilation flow (A) is activated to alleviate an obstruction or apneic event where the ventilation gas is delivered as a continuous flow 42.

Figure 8:
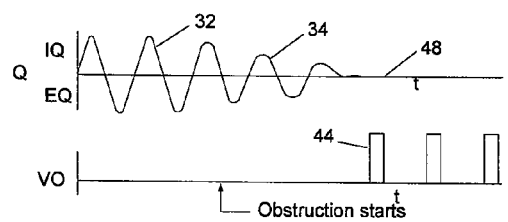
FIG. 8 is a graph showing when the transtracheal ventilation is activated to alleviate an obstruction or apneic event, where the ventilation gas is delivered at a periodicity that is predicted from past history of the patient's breath rate, or alternatively delivered at a predetermined rate and possibly asynchronous with the patient's breath effort.

FIG. 8 graphically describes an embodiment of the present invention where the transtracheal ventilation is activated to alleviate an obstruction or apneic event shown by an obstructed breath signal 48. The ventilation flow (A) may be delivered at a ventilator flow/volume at a rate based on past breath rate history 44. Alternatively, the ventilation flow (A) may be delivered at a predetermined rate and possibly asynchronous with the patient's breath effort.

Figure 9:
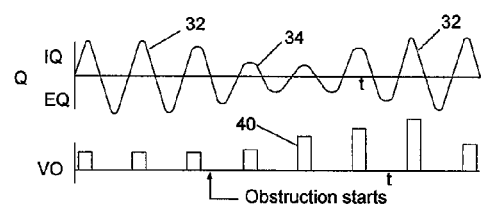
FIG. 9 is a graph showing when the transtracheal ventilation is activated to alleviate an obstruction or apneic event, where the ventilation gas is synchronized with the inspiratory phase of the breath cycle, and the ventilation gas delivery has variably increasing strength, such as volume, speed, or pressure, until alleviation of the obstruction is detected, at which time the ventilation gas delivery strength subsides.

FIG. 9 graphically describes embodiments of the present invention where the ventilation flow (A) is activated to alleviate an obstruction or apneic event. The ventilation flow (A) flow/volume may be synchronized with the inspiration 40 of the breath cycle, and the ventilation flow (A) may be delivered with variably increasing strength, such as volume, speed, or pressure, until it is detected that the obstruction is being alleviated, at which time the ventilation flow (A) delivery strength may subside.

Figure 10:
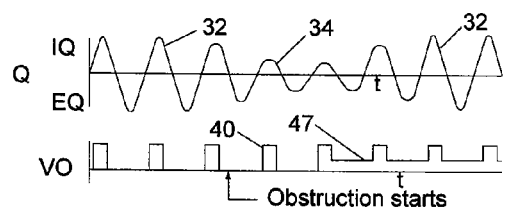
FIG. 10 is a graph showing when the transtracheal volume delivery is activated proactively to help prevent an obstruction or apneic event, where, when an obstruction or apneic event occurs, transtracheal ventilation gas flow alternates between volume deliveries during the inspiratory phase and continuous flow in-between volume deliveries.

FIG. 10 graphically describes embodiments of the present invention where the ventilation flow (A) flow/volume may be synchronized with the inspiration 40 of the breath cycle, and is activated proactively to help prevent an obstruction or apneic event. When an obstruction or apneic event occurs, the ventilation flow (A) flow may alternate between cyclical volume delivery 47 synchronized with the inspiratory phase, and continuous flow in-between volume deliveries.

Figure 11:
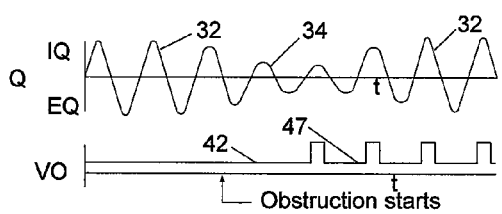
FIG. 11 is a graph showing when the transtracheal ventilation is activated proactively with continuous flow to help prevent an obstruction or apneic event or to help prevent desaturation, and where, when an obstruction or apneic event occurs, the transtracheal ventilation gas flow alternates between a volume delivery during the inspiratory phase, and a continuous flow in-between volume deliveries.

FIG. 11 graphically describes embodiments of the present invention where the ventilation flow (A) is activated proactively with continuous flow 42 to help prevent an obstruction or apneic event or to help prevent desaturation. When an obstruction or apneic event occurs, the ventilation flow (A) flow may alternate between a cyclic volume delivery 47 synchronized with the inspiratory phase, and continuous flow in-between volume deliveries.

Figure 12:
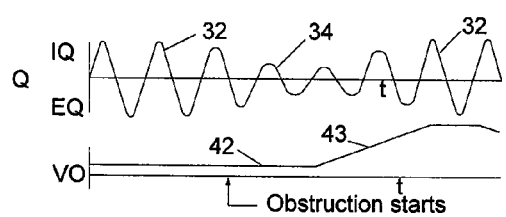
FIG. 12 is a graph showing when the transtracheal ventilation is activated proactively with continuous flow to help prevent an obstruction or apneic event or to help prevent desaturation, and wherein the amplitude of the continuous flow increases when an obstruction or apneic event is detected, and then subsides after the apneic event is corrected.

FIG. 12 graphically describes embodiments of the present invention where the ventilation flow (A) is activated proactively with continuous flow 42 to help prevent an obstruction or apneic event or to help prevent desaturation. The amplitude of the continuous flow 42 may increase as shown by the increasing ventilator continuous flow signal 43 when an obstruction or apneic event is detected, and then may subside after the apneic event is corrected.

Figure 13:
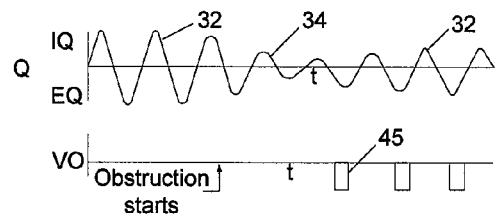
FIG. 13 is a graph showing when the transtracheal ventilation is activated to alleviate an obstruction or apneic event wherein the ventilation gas is delivered in synchronization with the patient's expiratory phase, and where the ventilation gas is delivered in a retrograde direction, i.e., away from the lungs and toward the oropharyngeal airway.

FIG. 13 graphically describes embodiments of the present invention where the ventilation flow (A) is activated to alleviate an obstruction or apneic event. The ventilation flow (A) may be delivered in synchronization with the patient's expiratory phase, and wherein the ventilation gas (A) volume may be delivered in a retrograde direction 45, that is away from the lungs and toward the oropharyngeal airway.

Figure 14A:
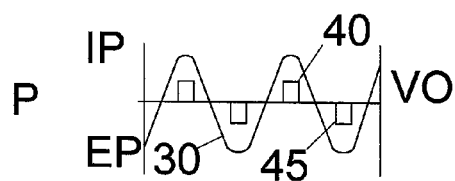
FIG. 14a is a graph showing when the transtracheal ventilation is synchronized to deliver augmentation to the lung during the inspiratory phase and augmentation in a retrograde direction toward the oropharyngeal airway during exhalation.

FIG. 14a graphically describes embodiments of the present invention where the ventilation flow (A) is synchronized to deliver ventilation toward the lung synchronized with inspiration 40 and ventilation in a retrograde direction 45 toward the oropharyngeal airway during exhalation.

Figure 14B:
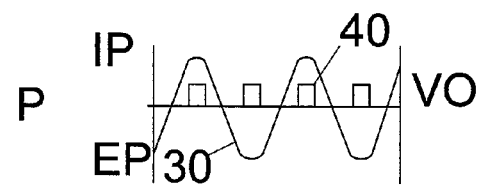
FIG. 14b is a graph showing when the transtracheal ventilation is synchronized to deliver augmentation to the lung during the inspiratory phase and during the expiratory phase.

FIG. 14b graphically describes embodiments of the present invention where the ventilation flow (A) is synchronized to deliver ventilation toward the lung synchronized with inspiration 40 and during the expiratory phase.

Figure 15A:
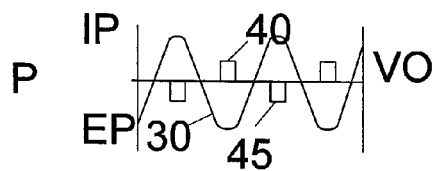
FIG. 15a is a graph showing when the transtracheal ventilation is synchronized to deliver augmentation to the lung during the expiratory phase and augmentation in a retrograde direction toward the oropharyngeal airway during the inspiratory phase.

FIG. 15a graphically describes embodiments of the present invention where the ventilation flow (A) is synchronized to deliver ventilation toward the lung synchronized with expiration 46 and ventilation in a retrograde direction 45 toward the oropharyngeal airway during the inspiratory phase.

Figure 15B:
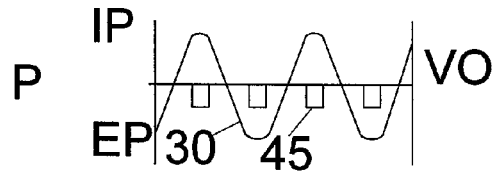
FIG. 15b is a graph showing when the transtracheal ventilation is synchronized to deliver augmentation in the retrograde direction toward the oropharyngeal airway during the inspiratory phase and during the expiratory phase.

FIG. 15b graphically describes embodiments of the present invention where the ventilation flow (A) is synchronized to deliver ventilation in the retrograde direction 45 toward the oropharyngeal airway during the inspiratory phase and during the expiratory phase.

Figure 16A:
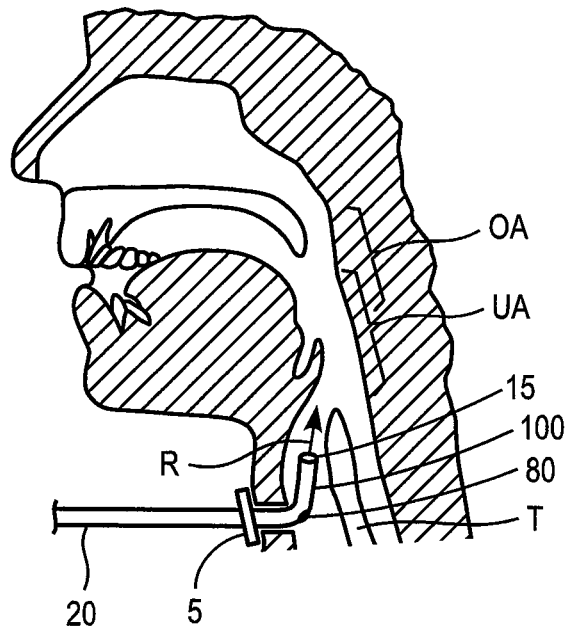
FIG. 16a is a diagram showing a retrograde transtracheal ventilation method and apparatus used to treat obstructive sleep apnea, in which ventilation gas is delivered in a retrograde fashion toward the oropharyngeal airway.

FIG. 16a describes another embodiment of the present invention with retrograde ventilation and a retrograde transtracheal catheter. Specifically, this embodiment describes a transtracheal ventilation method and apparatus used to treat OSA, in which ventilation gas is delivered in a retrograde direction or superiorly toward the oropharyngeal airway using a catheter with a gas exit port directed away from the lung toward the upper airway. This may be referred to herein as retrograde ventilation or "retrograde transtracheal ventilation" (RTV). Other names can also be used, such as "retrograde CPAP", "retrograde PAP", "retrograde AP", "retrograde synchronized ventilation", "retrograde jet ventilation", and/or "retrograde synchronized transtracheal jet ventilation". In RTV, the ventilator, gas delivery circuit, catheter and respiration sensor share the characteristics of the transtracheal ventilation method and apparatus described in FIGS. 2a-2d, with some exceptions.

A retrograde catheter 100 may be configured to deliver retrograde gas flow R in the superior direction from the trachea (T) towards the oropharyngeal airway (OA). The gas delivery parameters described previously, and the gas delivery timing functions described previously, also apply to RTV. For example, RTV can be applied as continuous flow, in synchrony with the inspiratory phase of the breath cycle, in synchrony with the expiratory phase of the breath cycle, at a predetermined back-up rate, at a rate based on previous breath rate history, at a relatively high frequency, and as combinations thereof. Also, RTV can be applied constantly, intermittently, proactively before an obstruction, while an obstruction is taking place, or after an obstruction or apneic event takes place. The respiration sensor may perform as described in previous embodiments, such as those shown in FIG. 2a.

The mechanism action of RTV may be proactive, predictive and/or reactive.

Proactive RTV: If RTV is employed proactively during normal breathing, before the onset of an upper airway obstruction, RTV can be delivered during the inspiratory cycle. The RTV flow rate delivered is a fraction of the patient's inspired flow rate, for example, approximately 5-75%, or preferably approximately 10-25% or approximately 4-10 LPM flow. Therefore, the patient's inspiration may dominate the retrograde flow and substantially inflates the lung despite some of the inspired flow being canceled by the retrograde flow. However, because the retrograde flow creates a counter resistance in the patient's airway between the mouth and catheter, the oropharyngeal airway is propped open by this counter resistance, and may prevent collapse of the structures in that area.

Predictive RTV: If RTV is employed when a partial obstruction occurs, the same principle applies. RTV may create counter resistance and a slight positive pressure at the oropharyngeal airway, and hence prop the structures open.

Reactive RTV: If RTV is employed when a substantially complete obstruction occurs, RTV may pressurize the closed airway between the catheter and the site of closure, and may open the closed structures and restore a flow path for breathing inspired air from ambient.

The drive pressure at the ventilator output for RTV is typically approximately 5-60 psi and preferably approximately 15-30, which creates a tracheal pressure of approximately 1-10 cmH2O under normal conditions, and can achieve tracheal pressures of up to approximately 15 cmH2O under partially obstructed conditions and up to approximately 20 cmH2O under fully obstructed conditions. The volumes, pressures and cycling rates and patterns of RTV delivery can be any of those described in embodiments associated with FIG. 2a and the associated graphs. In the descriptions thus far describing RTV, ventilation gas may be delivered during inspiratory phase; however, the gas can be delivered with the full variety of options described in the previous graphs and descriptions. The timing of delivery can be a critical factor in the efficacy of RTV. For example, the delivery can be at the beginning of the inspiratory cycle to prevent the collapse from occurring, or can be delivered slightly before the start of inspiration to begin to establish the flow dynamics needed to prop the structures open prior to the start of the next inspiratory cycle. RTV can potentially have the side effect of creating negative pressure in the lung and atelectasis, because or creating a venturi inferior to the gas exit port in the trachea (T). However, proper monitoring of the tracheal airflow and pressure, and using this information to alter the RTV parameters, may obviate the concern of negative lung pressure and atelectasis. The dual sensing embodiment described previously may also be applied to this embodiment.

Figure 16B:
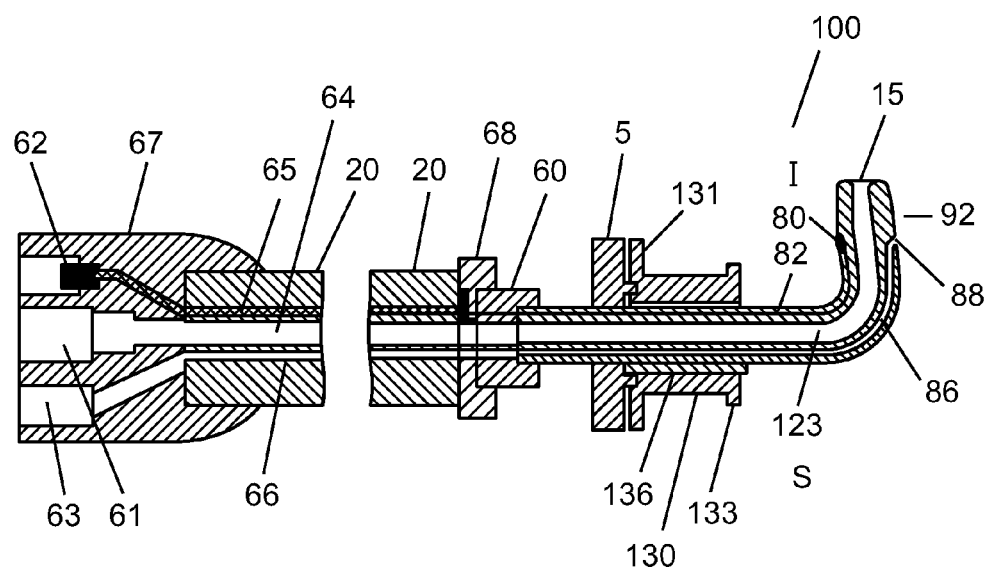

FIG. 16b illustrates the retrograde catheter of FIG. 2a in more detail. In this example, a stoma guide 130 is used. This is exemplary, however, and other structures may be used. The retrograde catheter 100 may include a pressure sensing lumen 88 and a pressure sensing port 86. Optionally, an active intratracheal respiration sensor 80, sensor wire 82 and a sensor wire lumen 84 may be used. The retrograde catheter 100 may be placed in the stoma guide 130 for positioning and securing the rotational alignment of the retrograde catheter 100. A ventilation catheter neck flange 5 can be secured to the stoma guide 130, if a stoma guide 130 is used, or directly to the neck if a stoma guide 130 is not used. If a stoma guide 130 is used, it is secured directly to the neck with a stoma guide strap 135. The catheter distal tip section 92 may include a catheter distal tip restriction 90 at its exit point to increase the speed of the gas exit velocity, if a venturi is the desired effect. A stoma guide keyway 136 and a ventilation gas delivery circuit 20 may be present.

Figure 17A:
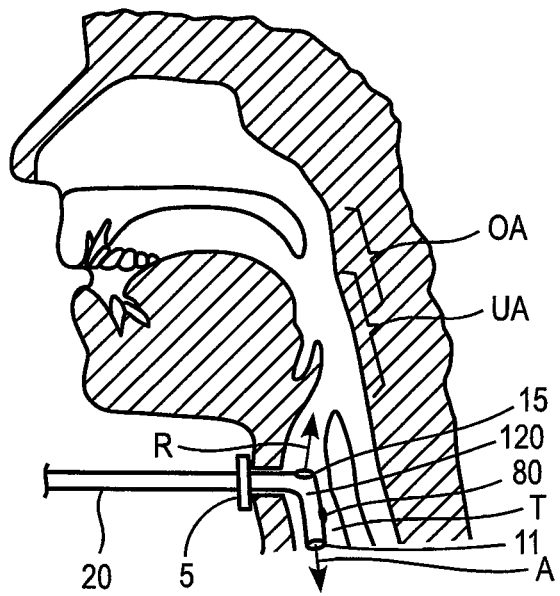
FIG. 17a is a diagram showing a transtracheal ventilation apparatus and method used to treat obstructive sleep apnea in which a ventilator and bidirectional transtracheal catheter are configured to deliver gas in both the direction of the lung and the oropharyngeal airway.
Figure 19A:
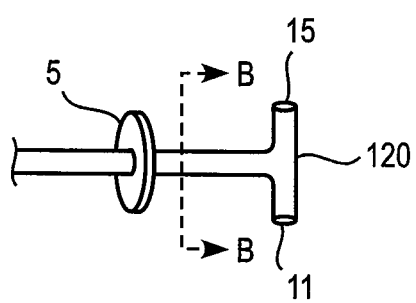
FIGS. 19a and 19b are diagrams showing a bidirectional ventilation catheter of FIG. 17a with two lumens and a bidirectional tip.
Figure 19B:
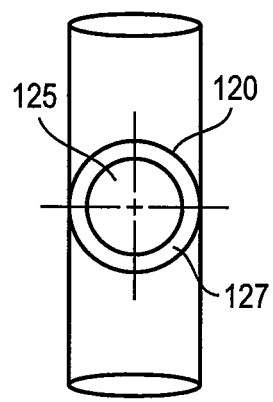
Figure 19C:
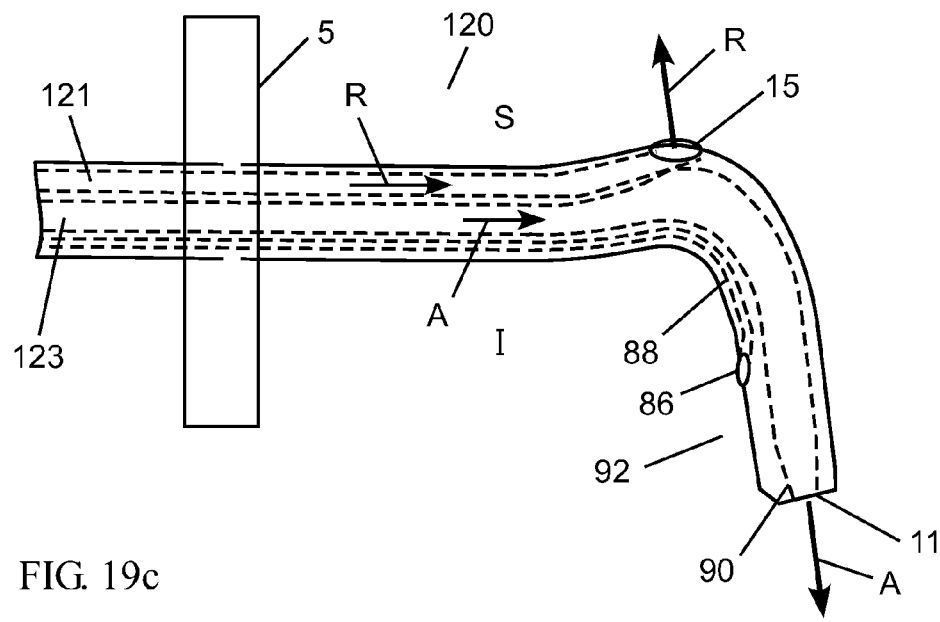
FIG. 19c is a diagram showing a bidirectional ventilation catheter of FIG. 17a with the distal tip curved inferiorly.

FIG. 17a describes another embodiment of the present invention which is a combination of the embodiments described in FIGS. 2 and 16, specifically transtracheal ventilation directed from the trachea (T) toward the lung (L) combined with RTV. In this case, the combined retrograde and normal direction ventilation catheter 120, which is a bi-directional-tipped catheter, and the ventilator (V) may have the ability to deliver ventilation gas both (1) from the trachea (T) toward the lung (L) via an inferior gas exit port 11, and (2) from the trachea (T) toward the oropharyngeal airway (OA) via superior gas exit port 15. This can be done as shown in FIGS. 19a and 19b with a combined retrograde and normal direction ventilation catheter 120 having a combined retrograde and normal direction gas delivery lumen 125.

The combined retrograde and normal direction gas delivery lumen 125 may be bifurcated at an inferior gas exit port 11 so that the gas flow is split into flow to the lung (A) and retrograde flow (R). In this case, the catheter distal tip material may be especially pliable, for example approximately 10-40 Shore A durometer, to compress the tip of the combined retrograde and normal direction ventilation catheter 120 so it can be inserted atraumatically. Or, preferably as shown in FIG. 18, the combined retrograde and normal direction ventilation catheter 120 may be divided into two gas delivery lumens, one as a gas delivery channel 121 and one as a gas delivery channel 123 to the lung (L). The two lumens 121, 123 are shown side by side, however, the two lumens 121, 123 can also be coaxial.

Figure 19D:
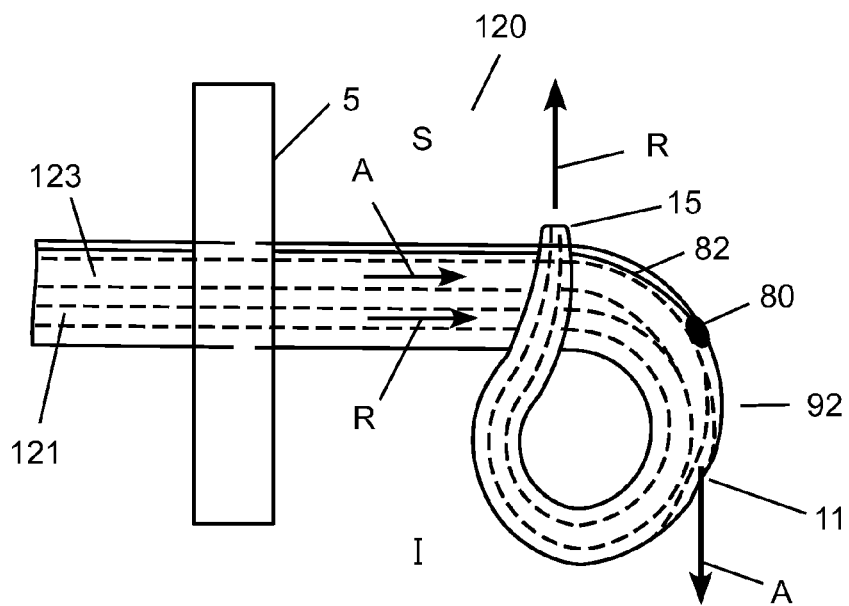
FIG. 19d is a diagram showing a bidirectional ventilation catheter of FIG. 17a with the distal tip curved greater than 210 degrees.

Alternate tip shapes and lumen configurations can be used. For example in FIG. 19c, a distal tip section is shown curved inferiorly, in contrast to the superior curve shown in FIGS. 18a and 18b, with a first orifice 11 for lung (L) ventilation flow at the end of the catheter, and a second orifice 15 for oropharyngeal airway (OA) flow near the center of the curve of the catheter. Or, as shown in FIG. 19d, the distal tip section of the catheter can be curved greater than approximately 210 degrees and preferably approximately 250-270 degrees, with a first orifice 11 formed near the approximately 80-90 degree region, and a second orifice 15 formed near the tip. Therefore, gas exiting the first orifice 11 is directed toward the lung (L) and gas exiting the second orifice 15 is directed toward the oropharyngeal airway (OA).

As in all other embodiments, the catheter can have a single gas delivery lumen and gas can alternate or be delivered simultaneously through both lumens, or the catheter can have multiple gas delivery lumens for dedicated lung and oropharyngeal directed airflow. The ventilation gas delivery characteristics, breath sensing and gas delivery timing are as described in other embodiments. The dual respiration sensing embodiment described earlier may also apply to this embodiment.

Figure 17B:
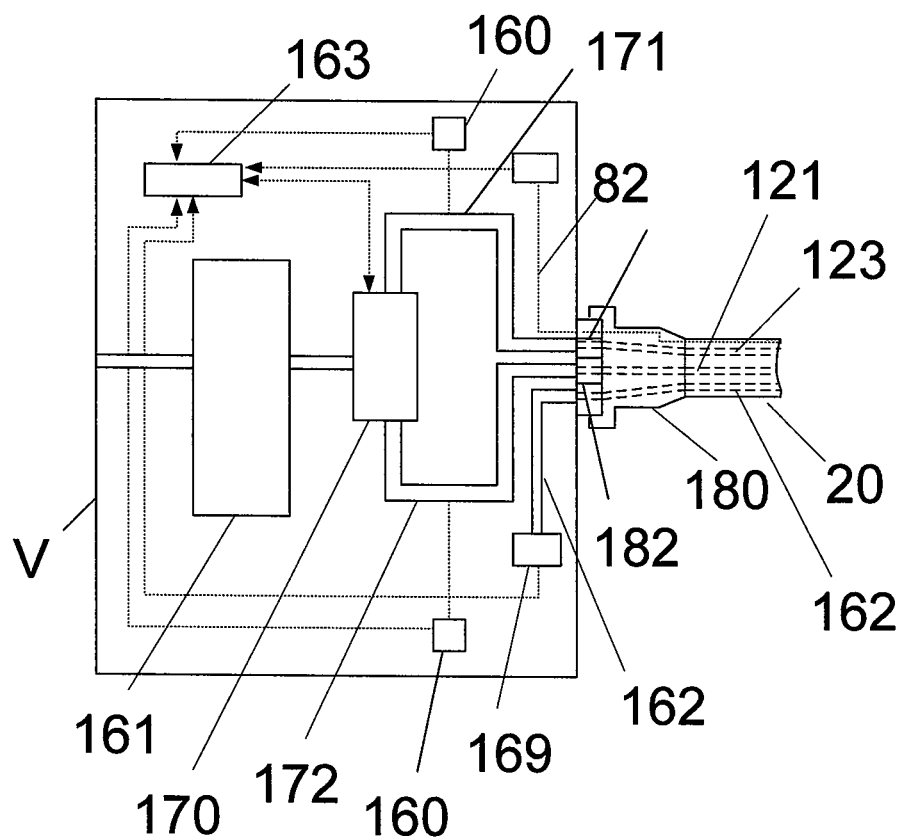
FIG. 17b describes the ventilator of FIG. 16a with the distal tip curved superiorly.
Figure 18A:
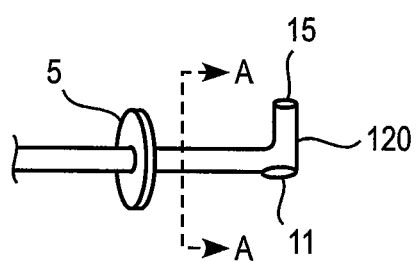
FIGS. 18a and 18b are diagrams showing a bidirectional ventilation catheter in which the catheter distal tip is curved in the direction of retrograde flow toward the oropharyngeal airway of FIG. 17a with two lumens used for the bidirectional flow.
Figure 18B:
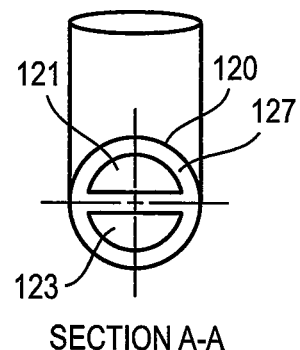

FIG. 17b describes the ventilator in more detail associated with FIG. 17a The ventilator (V) may include a dual control valve 170 with two outputs, a lung directed valve gas output 171, and a retrograde directed valve gas output 172. A ventilator (V) dual connector 180 for a gas delivery circuit may also include two gas outlet connections; a lung directed gas flow connector 181 and a retrograde directed gas flow connector 182. If a single gas delivery lumen is used for both lung flow (A) and retrograde flow (R) as shown in FIG. 19a, then only one gas outlet connection may be required between the ventilator and gas delivery circuit. A pressure monitoring line 162 may be in communication with a patient spontaneous respiration sensor 169.

Optionally, two lumens can be provided in the catheter, one lumen for flow toward the lung and one lumen for retrograde flow, and the ventilator gas output and tracheal pressure monitoring can alternate between the two lumens; for example, gas delivery in the retrograde lumen while tracheal pressure sensing in the other lumen, following by tracheal pressure sensing in the retrograde lumen while gas delivery in the other lumen.

FIGS. 20-23 graphically describe some examples of combining lung and retrograde ventilation. In this series of graphs, t is the time axis, Q is the airway flow signal, IQ is the inspiratory flow signal, EQ is the expiratory flow signal, VO is the ventilator output, A indicates ventilation gas directed toward the lung and R indicates ventilation gas directed retrograde toward the oropharynx, 32 is the normal breathing flow curve, and 34 is a breathing flow curve when the airway is partially obstructed.

Figure 20:
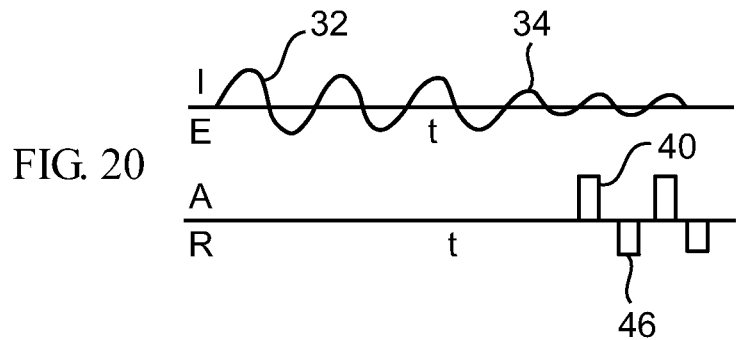
FIG. 20 is a graph showing when the transtracheal ventilation is activated to alleviate an obstruction or apneic event, where the augmentation flow to the lung is synchronized with the inspiratory cycle of the patient and the retrograde flow is synchronized with the expiratory cycle of the patient.

FIG. 20 graphically describes embodiments of the present invention where the transtracheal ventilation is activated to alleviate an obstruction or apneic event, wherein the ventilation flow (A) to the lung (L) is synchronized with inspiration 40 of the patient and the retrograde flow (R) is synchronized with exhalation 46 of the patient.

Figure 21:
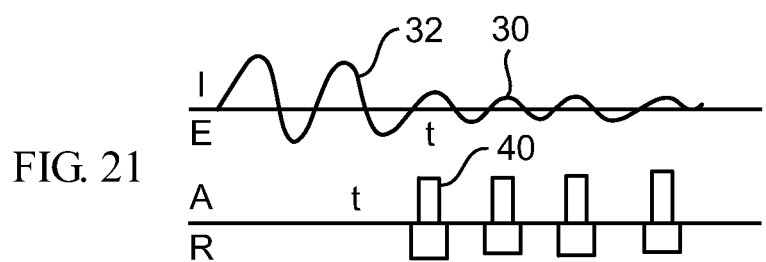
FIG. 21 is a graph showing when the transtracheal ventilation is activated to alleviate an obstruction or apneic event, where both the augmentation flow to the lung and the retrograde flow to the oropharyngeal airway are synchronized with the inspiratory cycle of the patient.

FIG. 21 graphically describes embodiments of the present invention where the transtracheal ventilation is activated to alleviate an obstruction or apneic event, wherein both the ventilation flow (A) to the lung (L) is synchronized with inspiration 40 of the patient and the retrograde flow 45 to the oropharyngeal airway (OA) are synchronized with the inspiratory cycle of the patient.

Figure 22:
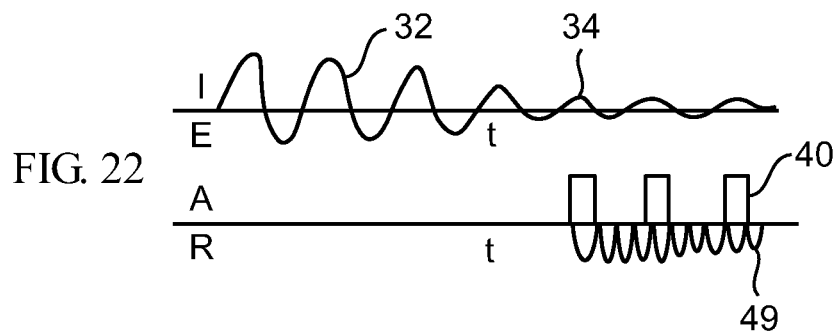
FIG. 22 is a graph showing when the transtracheal ventilation is activated to alleviate an obstruction or apneic event, where the augmentation flow to the lung is synchronized with the inspiratory cycle of the patient, and retrograde flow toward the oropharyngeal airway is delivered at a high frequency of volume oscillations.

FIG. 22 graphically describes embodiments of the present invention when the transtracheal ventilation is activated to alleviate an obstruction or apneic event, wherein the ventilation flow (A) to the lung (L) is synchronized with inspiration 40 of the patient, and the retrograde flow (R) toward the oropharyngeal airway (OA) is delivered as a retrograde high frequency volume delivery 49.

Figure 23:
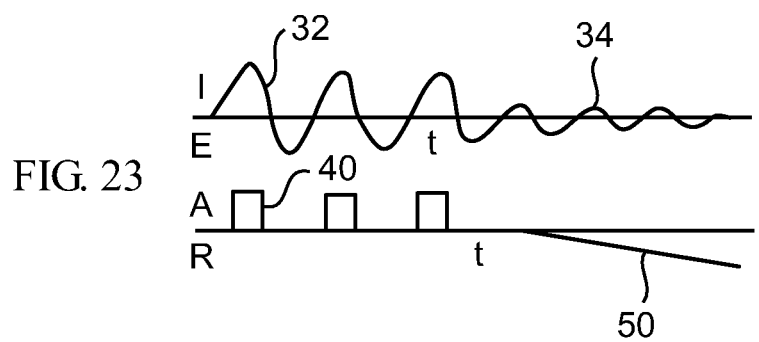
FIG. 23 is a graph showing when the transtracheal ventilation is activated to alleviate a potential obstruction or apneic event, where augmentation flow to the lung is synchronized with the inspiratory cycle of the patient during unobstructed breathing, and where retrograde continuously increasing flow is delivered toward the oropharyngeal airway.

FIG. 23 graphically describes embodiments of the present invention when the transtracheal ventilation is activated to alleviate a potential obstruction or apneic event, wherein the ventilation flow (A) to the lung (L) is synchronized with inspiration 40 of the patient during unobstructed breathing, and wherein retrograde ramping continuously increasing flow delivery 50 is directed toward the oropharyngeal airway (OA) during periods of reduced airflow signal 34.

It is noted again that in these embodiments where lung ventilation and retrograde ventilation are combined, all the possible variations described previously for gas delivery apply. For example, retrograde flow can be continuous flow, while lung ventilation can be delivered intermittently during an apneic period. Or, for example, retrograde gas delivery can be provided as a jet, while lung ventilation can be provided as a non-jet or vice versa. In general, the gas delivery parameters and the gas delivery timing functions, as well as the apparatus characteristics described previously in FIGS. 2 and 16 and the associated graphs apply to this combined embodiment.

Figure 24A:
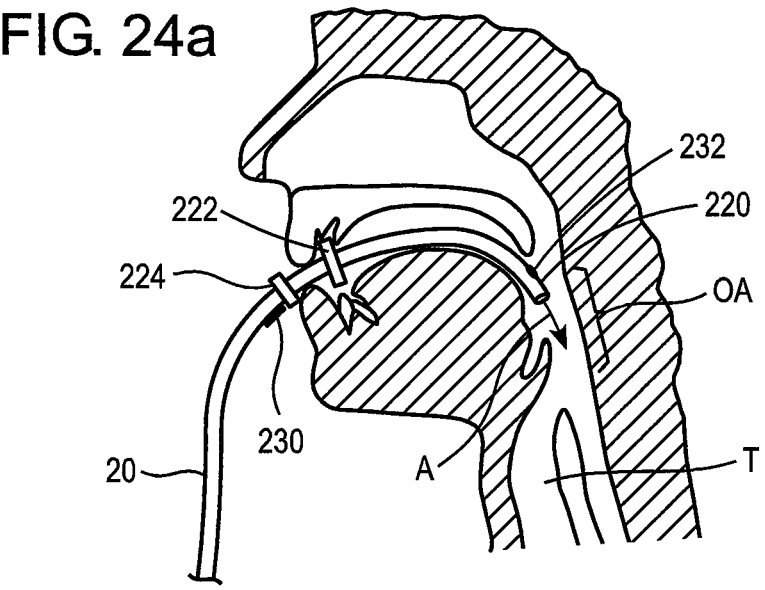
FIGS. 24a and 24b is a diagram showing a trans-oral ventilation method, ventilator and catheter used to treat sleep apnea.
Figure 24B:
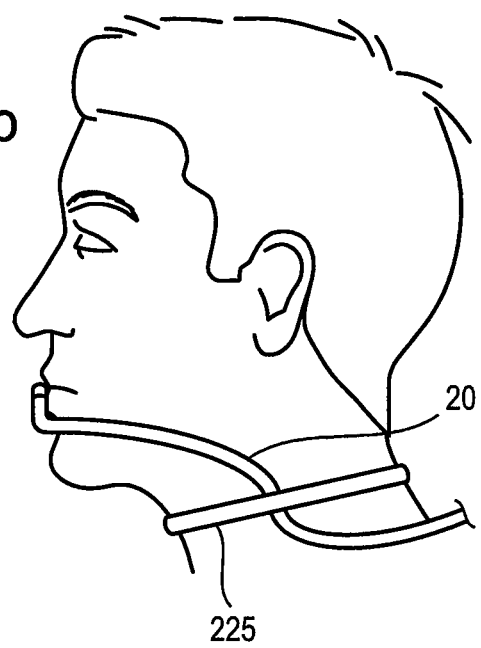

FIGS. 24*a* and 24*b* describe another embodiment of the present invention in which a trans-oral ventilation method and apparatus is used to treat sleep apnea. The ventilator (V), transtracheal catheter 10, breathing circuit characteristics, gas delivery and timing characteristics described in FIG. 2 may apply to this embodiment.

A trans-oral catheter 220 may include an intra-oral breath sensor 232, a lingual flange 222 on the lingual side of the teeth. Optional elements may include a buccal flange 224 on the buccal side of the teeth, and an external oral breath sensor 230. In addition, an external breath effort sensor can be combined with this embodiment. Therefore, during a partial or complete obstruction, the intra-oral or extra-oral breath sensor signal reduces in amplitude, while the breath effort sensor signal does not reduce significantly. The external breath effort sensor can be a thoracic sensor measuring dimensional excursions of the chest, or another type of neuromuscular sensor, or an esophageal sensor or another type of intra-airway sensor or implanted sensor. Inside the oral cavity, the trans-oral catheter 220 can be shaped to travel along the roof of the mouth, or on the top surface of the tongue, and/or along the lingual/medial side of the teeth or the buccal/lateral side of the teeth, or a combination of the above. The trans-oral catheter 220 may be inserted into the oral cavity to the depth of approximately the distal end of the hard palate. Optionally, the trans-oral catheter 220 may be inserted into the oropharyngeal cavity to the depth of between the start of the soft palate and the uvula. This depth is ample to direct the gas flow to the site of obstruction and to prevent or reduce collapse of the obstruction. The trans-oral catheter 220 can optionally be secured in position in the oral cavity with the aide of a very small and un-obtrusive oral appliance (not shown). Outside of the mouth, the trans-oral catheter 220 can be conveniently positioned on the user's head or face so that it is un-obtrusive when compared to CPAP, and optionally secured in place with a ventilation circuit neck strap 225.

Figure 25A:
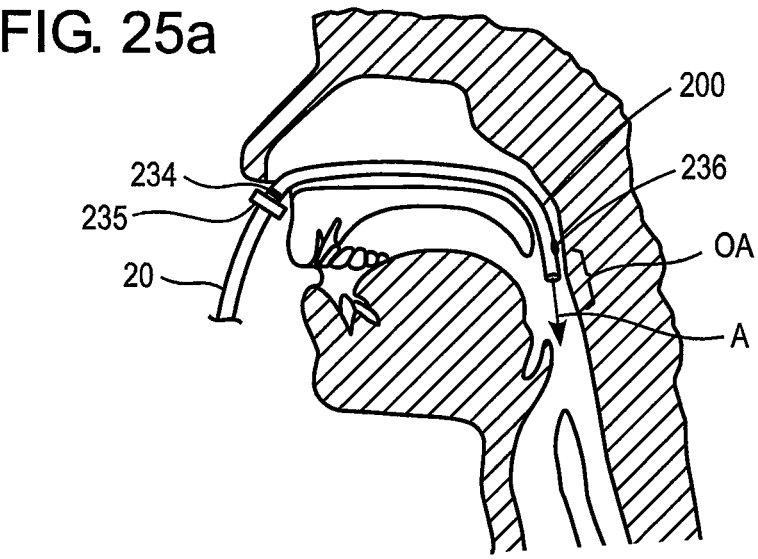
FIGS. 25a and 25b is a diagram showing a trans-nasal ventilation method, ventilator and catheter used to treat sleep apnea.
Figure 25B:
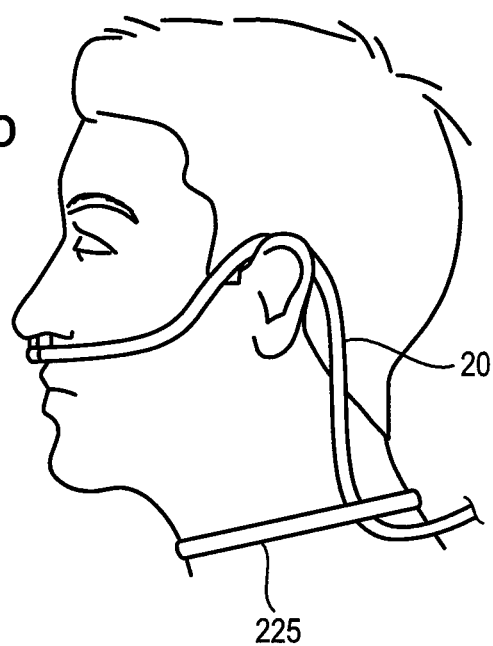

FIGS. 25*a* and 25*b* describe another embodiment of the present invention in which a trans-nasal ventilation method and apparatus is used to treat sleep apnea. The ventilator (V), transtracheal catheter 10 and breathing circuit characteristics, gas delivery and timing characteristics described in FIG. 2 may apply to this embodiment.

A trans-nasal catheter 200 may comprise an intra-nasal breath sensor 236. Optional elements may include a flange 235 near the septum of the nostrils, and optionally an external nasal breath sensor 234. In addition, an external breath effort sensor can be combined with this embodiment. Therefore, during a partial or complete obstruction, the intra-nasal or extra-nasal breath sensor signal reduces in amplitude, while the breath effort sensor signal does not reduce significantly. The external breath effort sensor can be a thoracic sensor measuring dimensional excursions of the chest, or another type of neuromuscular sensor, or an esophageal sensor or another type of intra-airway sensor or implanted sensor.

Inside the nasal cavity the trans-nasal catheter 200 can be placed along the roof of the nasal cavity, or along the bottom of the nasal cavity, in the midline or along the side, or a combination of the above. The trans-nasal catheter 200 can also be a semi-implanted such that it is attached to or partially or wholly implanted into the tissue inside the nasal cavity, preferably along the top of the palate. In any of the above cases, the depth of insertion of the trans-nasal catheter 200 may be approximately from the half way point of the palate to the end of the palate, or extending approximately 1 cm beyond the depth of the palate. This depth of insertion is adequate to direct the ventilation gas to the oropharyngeal airway (OA). Optionally, the trans-nasal catheter 200 may include, at a point proximal to the gas exit port, an enlarged diameter to increase the resistance to airflow through the nares. Preferably, the increase in diameter is a flange or cuff around the diameter of the trans-nasal catheter 200 near the nose, either inside the nose or near the nostrils. The feature can also be a flange or mask that is positioned outside the nostrils to both secure the catheter in place and seal the nostrils so that the ventilation gas does not leak out the nose. Optionally, this feature provides a partial or incomplete seal such that there is still a natural exhalation pathway out the nose in case the patient is not exhaling or can not exhale through the mouth.

Outside the nose, the trans-nasal catheter 200 can be conveniently positioned on the user's head or face so that it is un-obtrusive compared to CPAP, and optionally secured in place with a ventilation circuit neck strap 225. The catheter configuration may be similar to the characteristics described in FIGS. 24*a* and 24*b*.

The ventilation parameters used in the trans-nasal ventilation embodiment of FIGS. 25*a* and 25*b* may be similar to those parameters described in the foregoing in conjunction with the embodiment described in FIG. 2 and the associated graphs and descriptions, including timing, synchronization, volumes, pressures, gas compositions, amplitudes and waveform parameters.

It is noted that in the graphs the ventilator output waveform is typically shown square, however, other waveforms can be utilized with the invention, for example sinusoidal waveforms, accelerating waveforms, decelerating waveforms, and combinations thereof.

Figure 26:
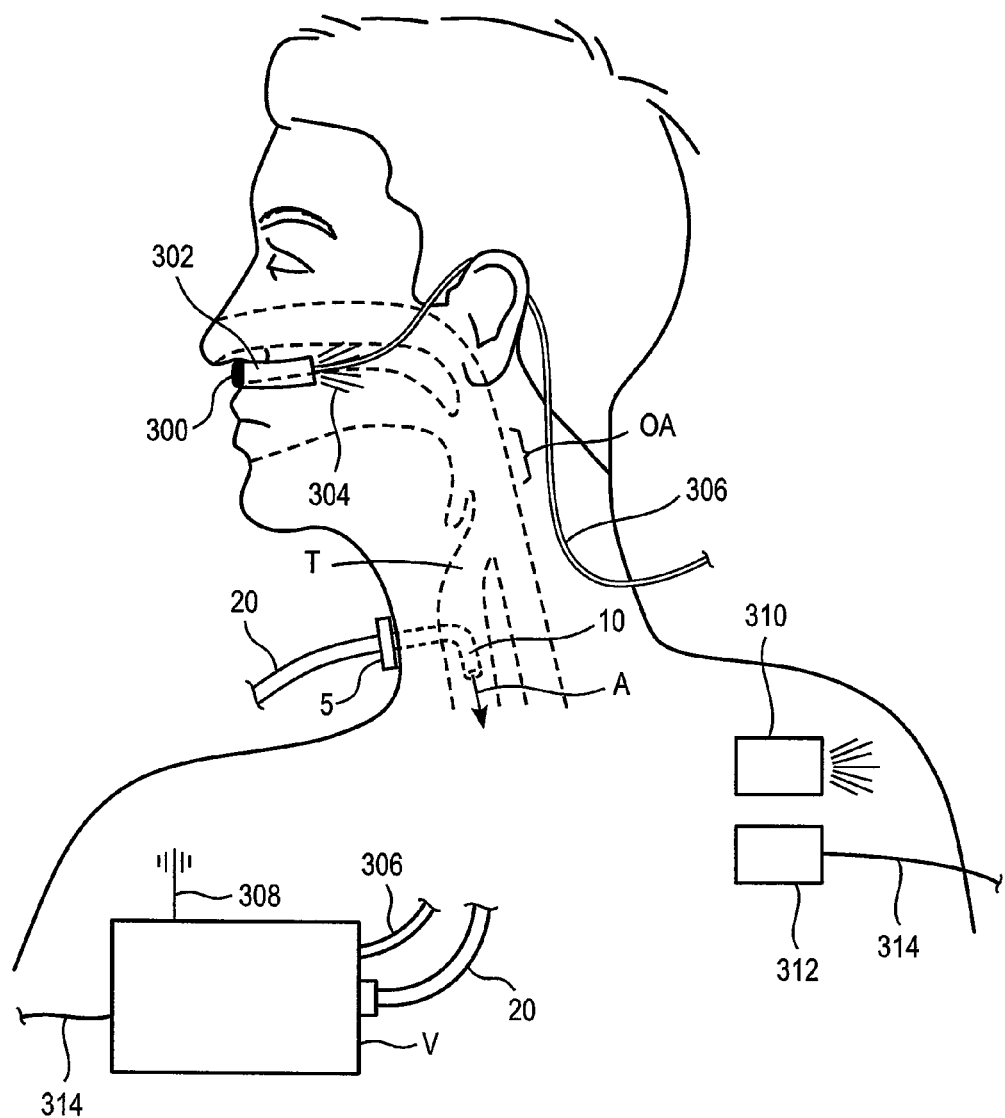
FIG. 26 is a diagram showing a transtracheal ventilation method, ventilator and catheter for treating OSA, including an external breath sensor to detect respiration and obstruction or apneic events.

FIG. 26 illustrates another embodiment of the present invention in which an external breath sensor 300 is used in conjunction with the embodiments described in FIGS. 2A, 16A and 17A. The ventilation delivery approach described in FIG. 26 is transtracheal ventilation, however trans-oral and trans-nasal ventilation also apply to this embodiment. In the example shown, the external airflow sensor 300 is an airflow sensor positioned under the nose and secured in place with an external airflow sensor securing tape or a head strap 302 or band. The external airflow sensor 300 can transfer information to the ventilator control system via an external airflow sensor wireless signal transmission 304. The external airflow sensor wireless signal transmission 304 may be received by a ventilation airflow sensor signal receiver 308, or via an external airflow sensor signal wire 306. The information from the external airflow sensor 300 may signal the ventilator (V) to provide ventilation as desired, during periods of apnea, partial obstruction, or other combinations described in the previous embodiments. The present embodiment may be advantageous in some circumstances such as light breathing or in chronic bronchitis when the airway has excessive secretions, in which case the intra-tracheal airflow sensors 80 may be less reliable than an external sensor. Additionally, included in this embodiment is a dual sensor approach in which the transtracheal catheter 10 may include a respiration sensor, especially useful for measuring breathing effort. The system may additionally include an external breath sensor, especially useful for measuring respiration airflow, to provide the overall system with a redundancy, and to be able to distinguish between breathing effort and actual breathing. The external airflow sensor can be a thermal sensor, a piezoelectric sensor, an ultrasonic sensor, a pneumotach sensor, a heated wire anemometer, as well as other types of sensing elements. While the external sensor is shown as a nasal or oral airflow sensor, this is exemplary and the external sensor can be any other type of sensor that measures actual respiration, such as gas composition sensor, pH sensor, and/or pulse oxymetry sensor.

In addition to the example in FIG. 26, the external breath sensor can be a breathing effort sensor rather than an actual respiration sensor. In this later case, an intra-airway sensor is an actual respiration sensor, such as a flow sensor or gas composition sensor. Examples of external breathing effort sensors are as described previously.

Another advantage of the present invention may be realized if the patient also suffers from respiratory insufficiency. In this case, the ventilation apparatus may be configured to be dual mode: during the daytime the patient may be administered transtracheal augmented ventilation, or trans-oral or trans-nasal augmented ventilation, using essentially the same ventilation apparatus and catheter. Then at night, the apparatus may be used for treating OSA, or for treating both OSA and respiratory insufficiency. In this case, the ventilator's therapeutic output parameters are likely different for OSA and respiratory insufficiency. Therefore, the ventilator (V) may include a convenient way for the user to switch from daytime mode to OSA mode. For example, a switch can be used to activate RTV. For example, the transtracheal catheter can be a dual gas delivery lumen, with a lung ventilation lumen and a retrograde lumen. During the day, the retrograde lumen is turned off, and before sleeping, the retrograde lumen and gas delivery controls on the ventilator is turned on. Daytime use for respiratory insufficiency in a first mode may use a first set of parameters including oxygen concentration, volume and pressure and timing output, and direction of airflow (inferior or superior). Nocturnal use during sleep in a second mode may use a second set of parameters including oxygen concentration, volume and pressure and timing output, and direction of airflow (inferior or superior). This dual mode example is exemplary, and all the possible combinations of gas delivery lumens, synchronization, retrograde directed flow and lung directed flow described earlier may use this aspect of the invention. Switching from daytime mode to OSA mode can also be automatic, controlled by a programmable internal clock in the ventilator, and controlled by an external input such as from the respiration sensor.

As part of the present invention, the ventilation gas delivered to the lung or the gas delivered in the retrograde direction can optionally be delivered using jet gas delivery dynamics. These dynamics can entrain airflow to amplify the effect from the ventilation gas itself. The exit speed can be approximately 25-300 m/s, and preferably approximately 100-200 m/sec. As described earlier, the gas delivery can be intermittent delivery of discrete volumes that have a therapeutic effect, or can be a high frequency rate creating pressure dynamics that have a therapeutic effect, or anti-obstruction or anti-collapse effect on the airway tissues and structures, such as high minute volume deliveries with low negative and positive pressure excursions. While in most cases it is desirable to adjust the ventilation parameters to maintain or restore patency of the upper airway, in some cases, it may be desired to close the upper airway with a venturi created by the catheter gas exit, to facilitate inflation of the lungs with the ventilator gas flow. Non-jet delivery is also included in the invention for example exit speeds below approximately 50 m/sec.

The gas composition delivered by the ventilator is typically normal air, since the patient may not require extra oxygen to maintain proper blood gas levels; however, the gas can be higher concentrations of oxygen by bleeding in oxygen from an oxygen source, such as a liquid oxygen source, compressed oxygen gas source, or an oxygen concentrator. Preferably, the oxygen concentration can be increased by allowing more oxygen to bleed into the gas delivery circuit using a control system controlled by the ventilator, in response to predicting or detecting an apnea event or obstruction. Therefore, the system can conserve oxygen when not needed, and use oxygen when most needed. Ideally, the system controls are configured to deliver approximately 21-35% oxygen when apneas or obstructions are not occurring and approximately 35-75% when apneas or obstructions are occurring.

In review of the invention, it should be noted that the invention addresses two aspects of treating OSA. The invention both provides ventilation to the lung from the ventilator, but also provides gas delivery to the obstruction to prevent, minimize or reverse obstruction thus restoring spontaneous breathing from ambient air. This has the additional advantage over conventional CPAP in that in CPAP the CPAP ventilation gas is both the gas used to open the obstruction and the gas used ventilate the lung. In this invention, transtracheal ventilation may be used to augment ventilation to the lung, and may also be used to open the obstruction so that the patient can breathe ambient air spontaneously. This can avoid the need for a heated humidifier that is required in CPAP, which is required to avoid drying of the upper airway because of the excessive gas being delivered by CPAP. Also, the gas delivery demands of this invention can be far less than that of CPAP, and hence the overall therapy can be quieter and the equipment can be packaged smaller which is useful for travel. Further, the patient interface, including the gas delivery circuit and catheter, may be smaller and lighter weight than CPAP therapy counterparts, making the therapy of this invention far less obtrusive and more tolerable by the user.

While the present invention is described in most of the examples to treat obstructive sleep apnea (OSA), with the appropriate modifications the invention can be applied to treat central sleep apnea (CSA), combinations of OSA and CSA, and other airway or breathing disorders. Further, the present invention can also be applied to other ventilation therapies or interventions such as anesthesia delivery, weaning from mechanical ventilation, emergency ventilation, oxygen therapy, therapeutic gas delivery, or drug delivery to name a few. Also, the transtracheal catheters included in the present invention can be inserted into a trachesotomy tube, in addition to a stoma guide or directly into the trachea. In addition, drug delivery can be included with the therapy, by including a drug delivery module in communication with the ventilator control system and gas delivery circuit. For example when an apneic event is predicted or detected, a drug which helps restore tissue rigidity to prevent tissue collapse can be delivered with the ventilation gas to the oropharyngeal airway.

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive.

The invention claimed is:

1. A ventilation apparatus for treating sleep apnea, the apparatus comprising:
   a ventilator for delivering ventilation gas;
   a control system for the ventilator;
   a trans-tracheal ventilation catheter for insertion a trachea;
   a distal tip on the trans-tracheal ventilation catheter;
   one or more first sensors, signals from the one or more first sensors measuring actual respiration;
   one or more second sensors, signals from the one or more second sensors measuring respiration effort;
   a ventilation gas delivery circuit connecting the ventilator to the trans-tracheal ventilation catheter;
   wherein a breathing cycle is determined by one or more signals from one or more of the one or more first sensors and the one or more second sensors; and
   wherein the control system activates the ventilator to deliver an increased volume of ventilation gas synchronized with the breathing cycle when apnea is detected by the one or more first sensors measuring a signal that is abnormally low and the one or more second sensors simultaneously measuring a signal that is not abnormally low.

2. The apparatus of claim 1, wherein the control system operates the ventilator such that ventilation gas is delivered in a manner selected from the group consisting of during an inspiration phase of the breathing cycle, during an expiration phase of the breathing cycle, during both an inspiration phase and an expiration phase of the breathing cycle, continuously during the breathing cycle, cyclically during the breathing cycle, with a flow amplitude that increases over time, with flow rates adjusted by the control system in response to measurements from the one or more first sensors and the one or more second sensors, and combinations thereof.

3. The apparatus of claim 1, wherein the ventilation gas is delivered at a low flow rate and a high pressure.

4. The apparatus of claim 1, wherein the ventilation gas is delivered at a high frequency.

5. The apparatus of claim 1, wherein the ventilation gas is delivered as a jet.

6. The apparatus of claim 1, wherein the ventilation gas is delivered in a manner selected from the group consisting of preemptively to prevent or minimize an obstruction or apneic event, while an obstruction or apneic event is developing, in reaction to an obstruction or apneic event, and combinations thereof.

7. The apparatus of claim 1, wherein the one or more first sensors and the one or more second sensors are coupled to the trans-tracheal ventilation catheter.

8. The apparatus of claim 1, wherein the one or more first sensors and the one or more second sensors are external to the trachea.

9. The apparatus of claim 1, wherein the one or more first sensors are one or more airflow sensors in the trachea and one or more pressure sensors in the trachea.

10. The apparatus of claim 9, wherein signals from the one or more airflow sensors and signals from the one or more pressure sensors are combined by the control system to activate the ventilator.

11. The apparatus of claim 1, further comprising a humidifier.

12. The apparatus of claim 1, wherein the trans-tracheal ventilation catheter is inserted through a stoma guide.

13. The apparatus of claim 1, wherein the distal tip curves superiorly towards the upper airway within the trachea.

14. The apparatus of claim 1, wherein the trans-tracheal ventilation catheter comprises multiple lumens with a function selected from the group consisting of delivering gas toward the lung, delivering gas toward the upper airway and away from the lung, monitoring pressure of the trachea, containing breath sensor wiring, or combinations thereof.

15. The apparatus of claim 1, wherein the distal tip comprises two ventilation gas exit ports, wherein a first gas exit port directs ventilation gas toward the lung and a second gas exit port directs gas superiorly away from the lung toward the upper airway.

16. The apparatus of claim 1, wherein the distal tip comprises a bifurcation, wherein a first part of the bifurcation is curved or angled inferiorly toward the lung and a second part of the bifurcation is curved or angled superiorly away from the lung toward the upper airway.

17. The apparatus of claim 1, wherein the ventilation apparatus operates in a first mode during daytime use for respiratory insufficiency using a first set of parameters and in a second mode during nocturnal used during sleep using a second set of parameters.

18. The apparatus of claim 1, wherein the ventilator is activated to deliver a first volume of ventilation gas synchronized with the breathing cycle when apnea is not detected and a second volume of ventilation gas synchronized with the breathing cycle when apnea is detected.

19. The apparatus of claim 18, wherein 10 ml to 200 ml of ventilation gas is delivered per ventilation cycle when apnea is not detected, and 200 ml to 500 ml of ventilation gas is delivered per ventilation cycle when apnea is detected.

20. The apparatus of claim 1, wherein the ventilator is activated to deliver a first composition of ventilation gas when apnea is not detected and a second composition of ventilation gas when apnea is detected.

21. The apparatus of claim 20, wherein the second composition of ventilation gas has a greater oxygen concentration than the first composition of ventilation gas.

22. The apparatus of claim 21, wherein the first composition of ventilation gas comprises 21 to 35% oxygen and the second composition of ventilation gas comprises 35 to 75% oxygen.

23. The apparatus of claim 1, wherein the ventilation gas is delivered at a low volume and a high frequency.

24. The apparatus of claim 23, wherein the low volume comprises a range of about 5 to 100 ml and the high frequency comprises a range of about 12 to 120 cycles per minute.

25. The apparatus of claim 23, wherein the low volume comprises a range of about 10 to 20 ml and the high frequency comprises a range of about 30 to 60 cycles per minute.

26. A method of treating sleep apnea, the method comprising:
inserting a trans-tracheal ventilation catheter with a distal tip into a trachea; measuring an actual patient respiration cycle with one or more first sensors and one or more second sensors, the one or more second sensors measuring patient respiratory effort;
controlling a ventilator with a control system based upon signals from the one or more of the one or more first sensors and the one or more second sensors;
selectively delivering ventilation gas from the ventilator to the trans-tracheal ventilation catheter through a ventilation gas delivery circuit in synchrony with the breathing cycle as measured by the one or more first sensors, an increased volume of ventilation gas being delivered when signals of the one or more first sensors is abnormally low and simultaneously when signals of the one or more second sensors is not abnormally low; and
wherein the distal tip of the trans-tracheal ventilation catheter directs the ventilation gas in a direction selected from the group consisting of superiorly from the trans-tracheal ventilation catheter towards an upper airway, inferiorly from the trans-tracheal ventilation catheter towards a lung, and combinations thereof.

27. The method of claim 26, wherein the control system operates the ventilator such that ventilation gas is delivered in a manner selected from the group consisting of during an inspiration phase of the breathing cycle, during an expiration phase of the breathing cycle, during both an inspiration phase and an expiration phase of the breathing cycle, continuously during the breathing cycle, cyclically during the breathing cycle, with a flow amplitude that increases over time, with flow rates adjusted by the control system in response to measurements from the one or more first sensors and the one or more second sensors, and combinations thereof thereof.

28. The method of claim 26, wherein the ventilation gas is delivered at a low flow rate and a high pressure.

29. The method of claim 26, wherein the ventilation gas is delivered at a high frequency.

30. The method of claim 26, wherein the ventilation gas is delivered as a jet.

31. The method of claim 26, wherein the ventilation gas is delivered in a manner selected from the group consisting of preemptively to prevent or minimize an obstruction or apneic event, while an obstruction or apneic event is developing, in reaction to an obstruction or apneic event, and combinations thereof.

32. The method of claim 26, wherein the one or more first sensors and the one or more second sensors are coupled to the trans-tracheal ventilation catheter.

33. The method of claim 26, wherein the one or more first sensors and the one or more second sensors are external to the trachea.

34. The method of claim 26, wherein the one or more first sensors are one or more airflow sensors in the trachea and one or more pressure sensors in the trachea.

35. The method of claim 26, further comprising a humidifier.

36. The method of claim 26, wherein the trans-tracheal ventilation catheter is inserted through a stoma guide.

37. The method of claim 26, wherein distal tip curves superiorly towards the upper airway within the trachea.

38. The method of claim 26, wherein the trans-tracheal ventilation catheter comprises multiple lumens with a function selected from the group consisting of delivering gas toward the lung, delivering gas toward the upper airway and away from the lung, monitoring pressure of the trachea, containing breath sensor wiring, or combinations thereof.

39. The method of claim 26, wherein the distal tip comprises two ventilation gas exit ports, wherein a first gas exit port directs ventilation gas toward the lung and a second gas exit port directs gas superiorly away from the lung toward the upper airway.

40. The method of claim 26, wherein the distal tip comprises a bifurcation, wherein a first part of the bifurcation is curved or angled inferiorly toward the lung and a second part of the bifurcation is curved or angled superiorly away from the lung toward the upper airway.

41. The method of claim 26, wherein the ventilation apparatus operates in a first mode during daytime use for respiratory insufficiency using a first set of parameters and in a second mode during nocturnal used during sleep using a second set of parameters.

42. A ventilation apparatus for treating sleep apnea, the apparatus comprising:
a ventilator for delivering ventilation gas;
a control system for the ventilator;
a ventilation catheter for placement into fluid communication with a patient airway;
a distal tip on the ventilation catheter;
one or more first sensors, signals from the one or more first sensors measuring actual respiration;
one or more second sensors, signals from the one or more second sensors measuring respiration effort;
wherein signals from the one or more first sensors and the one or more second sensors are combined to determine a breathing cycle;
a ventilation gas delivery circuit connecting the ventilator to the ventilation catheter;
wherein the control system operates the ventilator to deliver an increased volume of ventilation gas synchronized with the breathing cycle when apnea is detected by the one or more first sensors measuring a signal that is abnormally low and the one or more second sensors simultaneously measuring a signal that is not abnormally low; and
wherein the distal tip delivers the ventilation gas in a direction towards a lung.

43. The apparatus of claim 42, wherein the control system operates the ventilator such that ventilation gas is delivered in a manner selected from during an inspiration phase of the breathing cycle, during an expiration phase of the breathing cycle, during both an inspiration phase and an expiration phase of the breathing cycle, and combinations thereof.

44. The apparatus of claim 42, wherein the one or more first sensors measure actual respiration air movement, and the one or more second sensors directly or indirectly measure respiratory muscle effort, and wherein the control system processes the signals from the one or more first sensors and the one or more second sensors to distinguish conditions selected from the group consisting of light breathing, an obstruction, a reduced respiratory drive, and combinations thereof.

45. A method of treating sleep apnea, the method comprising;
    placing a ventilation catheter with a distal tip into fluid communication with a patient's airway;
    measuring a breathing cycle with one or more first sensors and one or more second sensors measuring patient respiratory effort;
    controlling a ventilator with a control system based upon signals from the one or more first sensors and the one or more second sensors;
    selectively delivering ventilation gas from the ventilator to the ventilation catheter through a ventilation gas delivery circuit in synchrony with the breathing cycle as measured by the one or more first sensors, an increased volume of ventilation gas being delivered when signals of the one or more first sensors is abnormally low and simultaneously when signals of the one or more second sensors is not abnormally low, low; and
    wherein the distal tip of the ventilation catheter directs the ventilation gas in a direction towards a lung.

46. The method of claim 45, wherein the control system operates the ventilator such that ventilation gas is delivered in a manner selected from during an inspiration phase of the breathing cycle, during an expiration phase of the breathing cycle, during both an inspiration phase and an expiration phase of the breathing cycle, and combinations thereof.

47. The method of claim 45, wherein the one or more first sensors measure actual respiration air movement, and the one or more second sensors directly or indirectly measure respiratory muscle effort, and wherein the control system processes the signals from the one or more first sensors and the one or more second sensors to distinguish conditions selected from the group consisting of light breathing, an obstruction, a reduced respiratory drive, and combinations thereof.

48. The method of claim 47, wherein the control system activates the ventilator to delivery ventilation gas if the one or more first sensors measure a signal that is abnormally low in amplitude, and the one or more second sensors simultaneously measure a signal that is not abnormally low in amplitude.

49. A ventilation apparatus for treating sleep apnea, the apparatus comprising:
    a ventilator for delivering ventilation gas;
    a control system for the ventilator;
    a trans-tracheal ventilation catheter for insertion into a trachea;
    one or more first sensors, signals from the one or more first sensors measuring actual respiration;
    one or more second sensors, signals from the one or more second sensors measuring respiration effort;
    wherein signals from the one or more first sensors and the one or more second sensors are combined to determine a breathing cycle; and
    a ventilation gas delivery circuit connecting the ventilator to the trans-tracheal ventilation catheter;
    wherein the control system operates the ventilator to deliver an increased volume of ventilation gas synchronized with the breathing cycle when apnea is detected by the one or more first sensors measuring a signal that is abnormally low and the one or more second sensors simultaneously measuring a signal that is not abnormally low.

50. The apparatus of claim 49, wherein the control system operates the ventilator such that ventilation gas is delivered in a manner selected from during an inspiration phase of the breathing cycle, during an expiration phase of the breathing cycle, during both an inspiration phase and an expiration phase of the breathing cycle and combinations thereof.

51. The apparatus of claim 49, wherein the one or more first sensors measure actual respiration air movement, and the one or more second sensors directly or indirectly measure respiratory muscle effort, and wherein the control system processes the signals from the one or more first sensors and the one or more second sensors to distinguish conditions selected from the group consisting of light breathing, an obstruction, a reduced respiratory drive, and combinations thereof.

52. A method of treating sleep apnea, the method comprising:
    inserting a trans-tracheal ventilation catheter into a trachea;
    measuring a breathing cycle with one or more first sensors and one or more second sensors measuring patient respiratory effort;
    controlling a ventilator with a control system based upon signals from the one or more first sensors and the one or more second sensors; and
    selectively delivering ventilation gas from the ventilator to the trans-tracheal ventilation catheter through a ventilation gas delivery circuit in synchrony with the breathing cycle as measured by the one or more first sensors and the one or more second sensors, an increased volume of ventilation gas being delivered when signals of the one or more first sensors is abnormally low and simultaneously when signals of the one or more second sensors is not abnormally low.

53. The method of claim 52, wherein the control system operates the ventilator such that ventilation gas is delivered in a manner selected from during an inspiration phase of the breathing cycle, during an expiration phase of the breathing cycle, during both an inspiration phase and an expiration phase of the breathing cycle, and combinations thereof.

54. The method of claim 52, wherein the one or more first sensors measure actual respiration air movement, and the one or more second sensors directly or indirectly measure respiratory muscle effort, and wherein the control system processes the signals from the one or more first sensors and the one or more second sensors to distinguish conditions selected from the group consisting of light breathing, an obstruction, a reduced respiratory drive, and combinations thereof.

* * * * *